US008044035B2

(12) United States Patent
Bartsch et al.

(10) Patent No.: US 8,044,035 B2
(45) Date of Patent: Oct. 25, 2011

(54) PHARMACEUTICAL COMPOSITIONS OF PYRIMIDINE-2,4,6-TRIONES

(75) Inventors: Pierre Bartsch, Liege (BE); Didier Cataldo, Trooz (BE); Richard Endele, Wilhelmsfeld (DE); Brigitte Evrard, Verlaine (BE); Jean-Michel Foidart, Trooz (BE); Hans-Willi Krell, Penzberg (DE); Gerd Zimmermann, Linkenheim (DE)

(73) Assignee: Universite De Liege, Angleur (BE)

( * ) Notice: Subject to any disclaimer, the term of this patent is extended or adjusted under 35 U.S.C. 154(b) by 91 days.

(21) Appl. No.: 12/472,775

(22) Filed: May 27, 2009

(65) Prior Publication Data
US 2010/0261672 A1 Oct. 14, 2010

Related U.S. Application Data

(63) Continuation of application No. 10/594,162, filed on Sep. 26, 2006, now abandoned.

(30) Foreign Application Priority Data

Apr. 1, 2004 (EP) ..................................... 04007921
Mar. 31, 2005 (WO) ................. PCT/EP2005/003348

(51) Int. Cl.
*A61K 31/515* (2006.01)
*A61K 31/724* (2006.01)
(52) U.S. Cl. ......................................... 514/58; 514/270
(58) Field of Classification Search .......................... None
See application file for complete search history.

(56) References Cited

U.S. PATENT DOCUMENTS

| | | | |
|---|---|---|---|
| 6,110,924 A | 8/2000 | Bosies et al. | |
| 6,242,455 B1 | 6/2001 | Grams et al. | |
| 6,350,786 B1 * | 2/2002 | Albano et al. | 514/772.4 |

FOREIGN PATENT DOCUMENTS

| | | |
|---|---|---|
| EP | 1 018 340 | 7/2000 |
| WO | WO 97/23465 | 7/1997 |
| WO | WO 98/58915 | 12/1998 |
| WO | WO 00/37109 | 6/2000 |
| WO | WO 00/40962 | 7/2000 |
| WO | WO 01/25217 | 4/2001 |
| WO | WO 02/089824 | 11/2002 |
| WO | WO 2005/097058 | 10/2005 |

OTHER PUBLICATIONS

Szente, L. et al "Highly soluble cyclodextrin derivatives . . . " Adv. Drug Deliv. Rev. (1999) vol. 36, pp. 17-28.*
Egeblad, M., and Werb, Z., Nat. Rev. Cancer 2 (2002) 161-174.
Overall, C.M., and Lopez-Otin, C., Nat. Rev. Cancer 2 (2002) 657-672.
Holmbeck, K., et al., Cell 99 (1999) 81-92.
Vu, T.H., et al., Cell 93 (1998) 411-422.
Shapiro, S.D., Curr. Opin. Cell Biol. 10 (1998) 602-608.
Lund, L.R., et al., EMBO J. 18 (1999) 4645-4656.
Carmeliet, P., et al., Nat. Genet. 17 (1997) 439-444.
Chang, C., and Werb, D., Trends Cell Biol. 11 (2001) S37-43.
Manes, S., et al., J. Biol. Chem. 274 (1999) 6935-6945.
Bergers, G., et al., Nat. Cell Biol. 2 (2000) 737-744.
Dong, Z., et al., Cell 88 (1997) 801-810.
Janowska-Wieczorek, A., et al., Blood 93 (1999) 3379-3390.
Carstanjen, D., et al., Transfusion 42 (2002) 588-596.
Grams, F., et al., Biol. Chem. 382 (2001) 1277-1285.
Ansel, H., et. al., Pharmaceutical Dosage Forms and Drug Delivery Systems, 6th ed., (1995), pp. 196 and 1456-1457.
Fabbri, L.M., and Hurd, S.S., Eur. Respir. J. 22 (2003) 1-2.
Higuchi, T., and Connors, K.A., Advances in Analytical Chemistry and Instrumentation 4 (1965) 117-212.
Yu, Z., and Westerlund, D., Chromatographia 44 (1997) 589-594.
Hubert, Ph., et al., S. T. P. Pharma Pratiques 9 (1999) 160-180.
Souverain, S., et al., Journal of Chromatography B 801 (2004) 141-156).
Chiap, P., et al., Journal of Chromatography B 817 (2005), 109-117.
Hubert, P., et al., Analytica Chimica Acta 391 (1999) 135-148.
Hubert, Ph., et al., S. T. P. Pharma Pratiques 13 (2003) 27-64.
Hubert, Ph., et al., J. Pharm. Biomed. Anal. 36 (2004) 579-586.
Hamelmann, E., et al., Am. J Respir. Crit. Care Med. 156 (1997) 766-775.
Cataldo, D.D., et al, Am. J. Pathol. 161 (2002) 491-498.
Aki, e t. al. Jour of Pharm Sci, V. 90 (2001) 1186-1197.
Csabai, Int Jour of Pharm 91 (1993) 15-22.
Foley, Bio & Med Chem Ltr (2001) 969-972.
Lopata, Jour of Phar Sci, 74 (1985) 211-213.
Mura, Eur Jour of Pharm (2005) 99-106.
Piel, Jour of Pharm Sci, 86 (1997) 475-480.
Szejtli, Cyclodextrin Tech (1988) 186-307.
Iwaoku, Chem Pharm Bull (1982) 1416-1421.
Loukas, Int Jour of Pharm 226 (2001) 207-211.
Suzuki, Chem Pharm Bull (1993) 1444-1447.
Lein, Oncogene (2002) 2089-2096.
Mura, Int Jour Pharm 260 (2003) 293-302.
Kumagai et al, *The Jour. of Immunology*, (1999) 162: 4212-4219.

* cited by examiner

*Primary Examiner* — Leigh Maier
(74) *Attorney, Agent, or Firm* — Jacobson Holman PLLC

(57) ABSTRACT

A trioxopyrimidine-cyclodextrin complex formed of a trioxopyrimidine derivative or a salt thereof and a water-soluble cyclodextrin derivative has improved solubility.

9 Claims, 11 Drawing Sheets

PHARMACEUTICAL COMPOSITIONS OF PYRIMIDINE-2,4,6-TRIONES

PRIORITY TO RELATED APPLICATION(S)

This application is a continuation of U.S. application Ser. No. 10/594,162, filed Sep. 26, 2006, now Pending,; which claims the benefit of European Application No. PCT/EP2005/003348 filed Mar. 31, 2005 and European Application No. 04007921.2 filed Jan. 4, 2004. The entire contents of the above-identified applications are hereby incorporated by reference.

The invention comprises a pharmaceutical composition of pyrimidine-2,4,6-triones (trioxopyrimidines), methods for the manufacture and uses thereof.

Matrix metalloproteases (MMPs) are a family of zinc- and calcium-dependent proteases that are capable of degrading the extracellular matrix (ECM) and basement membrane (Egeblad, M., and Werb, Z., Nat. Rev. Cancer 2 (2002) 161-174; Overall, C. M., and Lopez-Otin, C., Nat. Rev. Cancer 2 (2002) 657-672). They are believed to have pivotal roles in embryonic development and growth (Holmbeck, K., et al., Cell 99 (1999) 81-92; Vu, T. H., et al., Cell 93 (1998) 411-422) as well as in tissue remodeling and repair (Shapiro, S. D., Curr. Opin. Cell Biol. 10 (1998) 602-608; Lund, L. R., et al., EMBO J. 18 (1999) 4645-4656). Excessive or inappropriate expression of MMPs may therefore contribute to the pathogenesis of many tissue-remodelling processes, including tumor progression (Egeblad, M., and Werb, Z., Nat. Rev. Cancer 2 (2002) 161-174; Overall, C. M., and Lopez-Otin, C., Nat. Rev. Cancer 2 (2002) 657-672) and aneurysm formation (Carmeliet, P., et al., Nat. Genet. 17 (1997) 439-444). MMP effects are far from being restricted to ECM degradation (Chang, C., and Werb, D., Trends Cell Biol. 11 (2001) S37-43). Peptide growth factors that are sequestered by ECM proteins become available once degraded by MMP-9 (Manes, S., et al., J. Biol. Chem. 274 (1999) 6935-6945). MMPs can increase the bioavailability of VEGF (Bergers, G., et al., Nat. Cell Biol. 2 (2000) 737-744) but also generate angiogenesis inhibitors such as angiostatin by cleavage of plasminogen (Dong, Z., et al., Cell 88 (1997) 801-810). MMPs are thought to be involved in the mobilization of bone marrow stem cells (Janowska-Wieczorek, A., et al, Blood 93 (1999) 3379-3390). High concentration of MMP9 was observed during the G-CSF induced HPC mobilization (Carstanjen, D., et al., Transfusion 42 (2002) 588-596).

Trioxopyrimidines are compounds from a well-known structural class. Such compounds are described in, for example, U.S. Pat. Nos. 6,242,455 and 6,110,924; WO 97/23465; WO 98/58915; WO 01/25217, which are incorporated herein by reference, and Grams, F., et al., Biol. Chem. 382 (2001) 1277-1285, and are effective and highly selective for MMP-2, MMP-9 and MMP-14.

Cyclodextrins are cyclic carbohydrates derived from starch. They differ from one another by the number of glucopyranose units in their structure. The parent cyclodextrins contain six, seven and eight glucopyranose units, and are referred to as alpha, beta and gamma cyclodextrins respectively. The α-, β- or γ-cyclodextrins prepared by enzymatic starch conversion differ in the diameter of their hydrophobic cavity and are generally suitable for the inclusion of numerous lipophilic substances.

Trioxopyrimidines which are highly potent MMP inhibitors are only poorly soluble in water and water-based solvents. The object of the invention is therefore to provide an aqueous composition in which such a trioxopyrimidine is soluble and whereas such an aqueous composition of such a trioxopyrimidine can be used as a pharmaceutical composition.

SUMMARY OF THE INVENTION

It was surprisingly found that a trioxopyrimidine-cyclodextrin complex formed of a trioxopyrimidine derivative represented by the below-described formula (I) and a water-soluble cyclodextrin (further abbreviated as CD) exhibits enhanced water solubility, excellent stability, and low topical stimulation and is useful as a therapeutic agent.

It was furthermore found that such a trioxopyrimidine complex with cyclodextrin and an adjuvant such as L-lysine or L-arginine show improved water solubility and bioavailability, excellent stability, and low topical stimulation and is useful as a therapeutic agent. Accordingly, the present invention provides a trioxopyrimidine-cyclodextrin complex formed of a trioxopyrimidine derivative or a salt thereof and a cyclodextrin, preferably α-, β- or γ-cyclodextrin or a water-soluble cyclodextrin derivative (water-soluble being defined as a solubility of at least 0.5 gr/100 ml water at 25° C.), wherein the trioxopyrimidine derivative is represented by formula (I).

Furthermore the present invention provides a trioxopyrimidine-cyclodextrin complex formed of a trioxopyrimidine derivative represented by formula (I) or a salt thereof and a cyclodextrin, preferably α-, β- or γ-cyclodextrin or a water-soluble cyclodextrin derivative (water-soluble being defined as a solubility of at least 0.5 gr/100 ml water at 25° C.), in the presence of an adjuvant such as L-lysine or L-arginine, preferably L-lysine.

Such a complex according to the invention is an inclusion complex of trioxopyrimidine-cyclodextrin and is provided in a liquid or solid form.

In the complex according to the present invention, preferably 1 mol of trioxopyrimidine is complexed and enclosed by about 1 mol to 2 mol of cyclodextrin, preferably of β- or γ-cyclodextrin or a derivative thereof.

The present invention also provides a pharmaceutical agent for the treatment of a patient in the need thereof, preferably for the treatment of bronchial inflammatory diseases, containing a trioxopyrimidine-cyclodextrin complex according to the invention as an active component in a pharmaceutical effective amount.

The pharmaceutical agent according to the invention is applicable therapeutically, prophylactically or preventively, to pathologies resulting from a very important or unsuitable MMP expression. Preferably such treatment is a therapeutic, prophylactic or preventive treatment of rheumatoid arthritis, tumors, metastatic invasion, osteoporosis, macular degeneration, diabetic retinopathies, ulcerations of the cornea, atherosclerosis, bronchial inflammatory diseases, bronchial inflammatory diseases such as asthma, chronic obstructive pulmonary disease or emphysema.

The present invention also provides an injection formulation containing a trioxopyrimidine-cyclodextrin complex according to the invention in a pharmaceutically effective amount.

A further object of this invention is a liquid aqueous formulation of a complex according to the invention, the pharmaceutically acceptable carrier is water, the composition to administrate being an aqueous solution. The active substance according to the invention is then in the complex state by inclusion in a cyclodextrin in solution in water.

A further object of this invention is a liquid aqueous formulation of a complex according to the invention in the presence of L-Lysine (L-Lysine concentration between 10 mM and 1000 mM, preferably between 10 mM and 500 mM and more preferred between 10 mM and 100 mM) the pharmaceutically acceptable carrier is water, the composition to administrate being an aqueous solution. The active substance according to the invention is then in the complex state by inclusion in a cyclodextrin in solution in water in the presence of L-lysine.

A further object of this invention is a complex according to the invention in a solid state, the complex is in the form of a powder dissolvable in water and to dissolve before administration or to administrate on its own.

A further object of this invention is a complex included in different galenical forms according to the desired form of administration which can be tablets, capsules, multiparticulate systems, oral solutions, oral suspensions, solutions, suspensions, and implants for parenteral administration, solutions or powders for inhaling, hydrophilic or lipophilic type creams and ointments, aqueous or hydro-alcoholic gels, lotions, for topical, transcutaneous or vaginal use, intra-uterine devices, solutions, suspensions, implants, for ophthalmic use, suppositories, suspensions, sprays, solutions, and foams for rectal use.

The present invention further provides use of such a pharmaceutical agent in a pharmaceutically effective amount for the treatment of such diseases in a patient suffering from such a disease, preferably bronchial inflammatory diseases. The complex according to the invention is preferably administrated at a topical, percutaneous, transdermal, oral or parenteral level.

The present invention further provides a method for the manufacture of a pharmaceutical agent, preferably for the treatment of such diseases, preferably bronchial inflammatory diseases, characterized by complexing a trioxopyrimidine with cyclodextrin in a pharmaceutically effective amount in water or buffered aqueous solution preferably containing, in addition, an auxiliary substance, buffer, preservative, solvent and/or viscosity modulating agent.

The preferred cyclodextrins are alpha-cyclodextrin and its synthetic derivatives such as HPαCD, methylated αCD, hydroxybutyl αCD, maltosyl αCD, glucosyl αCD.

beta-cyclodextrin and its synthetic derivatives such as HPβCD, SBEβCD, RMβCD, DIMEβCD, TRIMEβCD, hydroxybutyl βCD, glucosyl βCD, maltosyl βCD.

gamma-cyclodextrin and its synthetic derivatives such as HPγCD, RMγCD and DIMEγCD, hydroxybutyl γCD, glucosyl γCD, maltosyl γCD.

This invention also concerns use of a pharmaceutical composition including, in a therapeutically effective quantity, a pyrimidine-2,4,6-trione and at least one cyclodextrin, as well as possibly a pharmaceutically acceptable carrier, for the manufacture of a medicine for a therapeutic, prophylactic or preventive treatment of the above-mentioned illnesses.

This invention also concerns use of a pharmaceutical composition including, in a therapeutically effective quantity, a) a pyrimidine-2,4,6-trione, b) at least one cyclodextrin c) L-lysine or L-arginine, preferably L-lysine, as well as d) possibly a pharmaceutically acceptable carrier, for the manufacture of a medicine for a therapeutic, prophylactic or preventive treatment of the above-mentioned illnesses.

DETAILED DESCRIPTION OF THE INVENTION

Pyrimidine-2,4,6-triones (trioxopyrimidines) according to the present invention are those of formula (I)

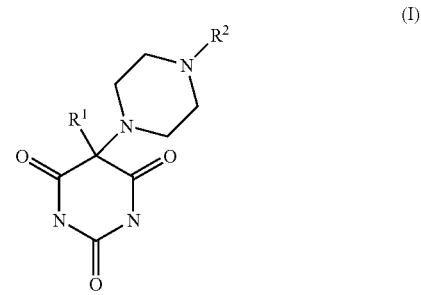

(I)

wherein $R^1$ is $C_3$-$C_{20}$ alkyl, which may optionally be interrupted once or several times by —S—, —O— or —NH—; or a group W-V, wherein W is a chemical bond or phenyl; and V is phenyl, phenyloxy, phenylthio, phenylsulfinyl, phenylsulfonyl or phenylamino, which phenyl moieties may be unsubstituted or substituted once or several times by halogen, hydroxy, $C_1$-$C_6$ alkyl, $C_1$-$C_6$ alkoxy, $C_1$-$C_6$-alkylthio, $C_1$-$C_6$ alkylsulfinyl, $C_1$-$C_6$-alkylamino, cyano, nitro or $C_1$-$C_6$-alkylsulfonyl; and $R^2$ is $C_1$-$C_{10}$ alkyl, which alkyl group is unsubstituted or substituted one or two times by hydroxy or amino and may optionally be interrupted once or several times by —S—, —O— or —NH—;

a benzoyl group, which may be unsubstituted or substituted once or several times by halogen, hydroxy, nitro, $C_1$-$C_6$-alkoxy, $C_1$-$C_6$-alkylamino, $C_1$-$C_6$-alkylthio, $C_1$-$C_6$-alkylsulfinyl, $C_1$-$C_6$-alkylsulfonyl, amidosulfonyl, $C_1$-$C_6$-alkylamidosulfonyl, bis-$C_1$-$C_6$-alkylamido-sulfonyl;

a heteroaromatic acyl group; or a phenyl- or heteroaryl group, which are unsubstituted or substituted once or several times by halogen, hydroxy, $C_1$-$C_6$-alkoxy, $C_1$-$C_6$-alkylamino, $C_1$-$C_6$-dialkylamino, cyano, $C_1$-$C_6$-alkyl, $C_2$-$C_6$ alkenyl, $C_2$-$C_6$-alkinyl, $C_1$-$C_6$-acyl, $C_1$-$C_6$-alkylthio, $C_1$-$C_6$-alkylsulfonyl, $C_1$-$C_6$-alkylsulfinyl, $C_1$-$C_6$-alkylaminocarbonyl, aminocarbonyl, $C_1$-$C_6$-alkylamidosulfonyl, amidosulfonyl, bis-$C_1$-$C_6$-alkylamidosulfonyl, nitro, $C_1$-$C_6$-alkoxycarbonyl, carboxy.

An object of the present invention is the use of the compounds of formula (I), as well as their pharmaceutically acceptable salts, enantiomeric forms, diastereoisomers and racemates, in the manufacture of novel pharmaceutical preparations.

As used herein for $R^1$, the term "$C_3$-$C_{20}$ alkyl" represents a linear or a branched saturated hydrocarbon containing from 3 to 20-, preferably from 4 to 12- and more preferably from 8 to 12 carbon atoms. Examples are butyl, hexyl, octyl, decyl, 2-ethylhexyl, 2 ethyloctyl. Preferred $C_3$-$C_{20}$ alkyl residues are n-octyl and n-decyl. The $C_3$-$C_{20}$ alkyl group may be interrupted once or several times by —S—, —O— or —NH—, preferably by —O—. Examples for such $C_3$-$C_{20}$ alkyl groups are 5-ethoxy-n-pentyl, 9-methoxy-n-octyl.

The substituents in the phenyl moieties of "V" are preferably located in p- and/or meta-position.

Preferably the group "W-V" is p-butoxyphenyl, biphenyl, phenoxyphenyl, p-chloro-phenoxyphenyl, p-bromo-phenoxyphenyl, 3,4 dichloro-phenoxyphenyl.

The term "$C_1$-$C_{10}$-alkyl" as used in $R^2$ represents a linear or branched saturated hydrocarbon, containing from 1 to 10, preferably from 1 to 6 and more preferably from 1 to 4 carbon atoms. Said $C_1$-$C_{10}$-alkyl may be interrupted once or several times by —S—, —O— or —NH—, preferably by —O— and more preferably in such a way to give a group which is composed of ethyleneoxy fragments. Preferred examples of $C_1$-$C_{10}$-alkyl groups are hydroxyethyl; hydroxypropyl; ethoxyethyl; 1,2-bisethoxyethyl; 1,2-bis-hydroxy-ethyl.

The term heteroaromatic as used in "heteroaromatic acyl group" in $R^2$ denotes a five- or six membered aromatic ring, wherein one, two or three ring atoms are oxygen, nitrogen or sulfur, and the remaining ring atoms being carbon atoms. Said heteroaromatic group may be fused to another phenyl ring. Examples for such heteroaromatic acyl groups are furanecarboxyl, thiophenecarboxyl, 4-imidazolylcarboxyl, 3-benzthiophenecarboxyl, pyridylcarboxyl. Preferred examples are furanecarboxyl and thiophenecarboxyl.

The term "heteroaryl" as used herein means heteroaromatic as defined above. Preferred heteroaryl groups are electron deficient residues such as the nitrogen containing 6-membered rings like pyridine, pyrimidine, pyrazine or 1,3, 5-triazine. Especially preferred are the heteroaryl groups pyrimidinyl or pyrazinyl.

Substituents which may be present on the phenyl or heteroaryl groups of $R^2$ are principally located at any position suitable for the respective substitution reaction. Preferably one or two substituents are present in para and/or meta position.

The term "$C_1$-$C_6$-alkyl" as used herein alone or in combination with $C_1$-$C_6$-alkoxy, $C_1$-$C_6$-alkylamino, $C_1$-$C_6$-dialkylamino, $C_1$-$C_6$-acyl, $C_1$-$C_6$-alkylthio, $C_1$-$C_6$-alkylsulfonyl, $C_1$-$C_6$-alkylsulfinyl $C_1$-$C_6$-alkylaminocarbonyl, $C_1$-$C_6$-alkylamidosulfonyl, bis-$C_1$-$C_6$-alkylamidosulfonyl or $C_1$-$C_6$-alkoxycarbonyl denotes a linear or branched, saturated hydrocarbon with 1 to 6-, preferably 1 to 4 carbon atoms. Preferred examples are methyl, ethyl, propyl, isopropyl or tert.-butyl.

The term "$C_2$-$C_6$-alkenyl" as used herein denotes a linear or branched unsaturated hydrocarbon containing 2 to 6-, preferably 2 to 5 carbon atoms and one or two double bonds. If two double bonds are present they can be isolated- or conjugated double bonds, preferably conjugated double bonds. Preferred examples are allyl or pentadienyl.

The term "$C_2$-$C_6$-alkinyl" as used herein denotes a linear or branched hydrocarbon containing 2 to 6-, preferably 2 to 4 carbon atoms. The preferred example is propargyl.

The term "halogen" means fluorine, chlorine, bromine, iodine, preferably chlorine or bromine.

The term "several times" as used herein means one, two, three or four times, preferably one or two times.

The term "pharmaceutically acceptable salt" as used herein before refers to conventional acid-addition salts or base-addition salts that retain the biological effectiveness and properties of the compounds of formula (I) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds (see, e.g., Ansel, H., et. al., Pharmaceutical Dosage Forms and Drug Delivery Systems, 6th ed., (1995), pp. 196 and 1456-1457).

The compounds of the present invention can be prepared as described in EP 0 869 947 and WO 01/25217.

According to the invention, the following compounds are particularly preferred:
5-Biphenyl-4-yl-5-[4-(4-nitro-phenyl)-piperazin-1-yl]pyrimidine-2,4,6-trione
(Compound I)
5-(4-Phenoxy-phenyl)-5-(4-pyrimidin-2-yl-piperazin-1-yl)-pyrimidine-2,4,6-trione
(Compound II)
5-[4-(4-Chloro-phenoxy)-phenyl]-5-(4-pyrimidin-2-yl-piperazin-1-yl)-pyrimidine-2,4,6-trione
(Compound III)
5-[4-(3,4-Dichloro-phenoxy)-phenyl]-5-(4-pyrimidin-2-yl-piperazin-1-yl)-pyrimidine-2,4,6-trione
(Compound IV)
5-[4-(4-Bromo-phenoxy)-phenyl]-5-(4-pyrimidin-2-yl-piperazin-1-yl)-pyrimidine-2,4,6-trione
(Compound V).

It is also apparent that when the trioxopyrimidine derivative (I) contains an acidic moiety such as a carboxylic group or a sulfonyl group, the derivative can form a salt with a base via the acidic moiety.

In addition to the above-described adduct-type salt, the trioxopyrimidine may take a hydrate form or a solvated form. The hydrate and the solvate include both that of the free compound of the formula (I) and a salt of the compound of the formula (I). They also include a tautomer of the compound of the formula (I).

Cyclodextrins (CD) according to the invention are cyclic oligosaccharides produced by enzymatic degradation of starch, which are composed of a variable number of glucopyrannose units, mostly 6, 7 or 8: these cyclodextrins are respectively named α, β, and γ cyclodextrins (αCD, βCD and γCD). Cyclodextrins according to the invention are cyclodextrins per se or cyclodextrin derivatives, which are at least water soluble in an amount of 0.5 gr/100 ml at 25° C.

The water-soluble cyclodextrin preferably used in the present invention refers to a cyclodextrin having water solubility of at least that of β-cyclodextrin. Examples of such water-soluble cyclodextrin are sulfobutylcyclodextrin, hydroxypropyl-cyclodextrin, maltosylcyclodextrin, and salts thereof. In particular, sulfobutyl-β-cyclodextrin, hydroxypropyl-β-cyclodextrin, maltosyl-β-cyclodextrin, and salts thereof.

Cyclodextrins preferred according to the invention are also methylcyclodextrins (products of the cyclodextrins methylation), dimethylcyclodextrins (DIMEB) (preferably substituted in 2 and in 6), trimethylcyclodextrins (preferably substituted in 2, 3 and 6), "random methylated" cyclodextrins (preferably substituted at random in 2, 3 and 6, but with a number of 1,7 to 1,9 methyl by unit glucopyrannose, RMβCD), hydroxypropylcyclodextrins (HPCD, hydroxypropylated cyclodextrins preferably substituted randomly mainly in position 2 and 3 (HP-βCD, HP-γ CD)), sulfobutylethercyclodextrins (SBECD), hydroxyethyl-cyclodextrins, carboxymethylethylcyclodextrins, ethylcyclodextrins, amphiphilic cyclodextrins obtained by grafting hydrocarbonated chains in the hydroxyl groups and being able to form nanoparticles, cholesterol cyclodextrins and triglycerides-cyclodextrins obtained by grafting cyclodextrins monoaminated (with a spacer arm).

Adjuvants according to the invention are L-lysine or L-arginine, preferably L-lysine. Such adjuvants can be used to increase the solubility of acidic components by ternary complex formation. The trioxopyrimidine-cyclodextrin complex of the present invention may be obtained by producing an aqueous solution containing the trioxopyrimidine or a salt thereof and a water-soluble cyclodextrin. The water-soluble cyclodextrin is used in an amount of preferably one mol or more based on 1 mol per mol trioxopyrimidine or a salt thereof, more preferably 1-10 mol, and particularly preferably 1-2 mol cyclodextrin per mol trioxopyrimidine.

The higher the concentration of the water-soluble cyclodextrin, the more the solubility of the trioxopyrimidine increases. No particular limitation is imposed on the method for producing the aqueous solution, and for example it is produced by use of water or a buffer in a temperature range approximately from −5 to 35° C.

When a cyclodextrin aqueous solution is stirred with an excess of a trioxopyrimidine of formula I, there is a complex formation between these two molecules. Reaching the equilibrium takes, however, about at least a few days, so that after a few hours or even after one day, the improved solubility of trioxopyrimidines according to the invention is not found. The filtration of the solution allows recovering the complex in solution in the filtrate, the complex being soluble in water. The complex can also be obtained by mixing a solubilized known quantity of a trioxopyrimidine of formula I in aqueous solution with a solubilized known quantity of CD by calculating the adequate proportions.

Another way of obtaining a complex is to add a solution of a trioxopyrimidine of formula I in a solvent (e.g. alcohol, acetone, etc) to a cyclodextrin aqueous solution. The complex can be formed after sufficient stirring, either after evaporation of the solvent, or even in the presence of the solvent.

In all these methods of obtaining a trioxopyrimidine-CD complex, a solution of L-Lysine or L-Arginine (amino acid concentration between 10 mM and 1000 mM, preferably between 10 mM and 500 mM and more preferred between 10 mM and 100 mM) can be used as adjuvant. A solution of L-lysine is preferred as adjuvant.

The lyophilization or the nebulization of solutions of the complex according to the invention allows the complex to be obtained in solid form. One can thus obtain a complex in the form of an amorphous powder. It is also possible to obtain the complex in the solid state after dissolution of CD and a trioxopyrimidine of formula I in an appropriate organic solvent and further evaporation of the solvent.

Other methods can be used for solid complexes preparation which are violent stirring of a suspension of a trioxopyrimidine of formula I and CD in a very small quantity of water, then complex collecting after drying or the use of $CO_2$ in a supercritical state for mixing a trioxopyrimidine of formula I and CD in presence of $CO_2$ in a supercritical state.

The complex according to the present invention can be prepared, for example, in a manner known per se from a solution or using the paste method, where the weight ratio of cyclodextrin to trioxopyrimidine should be between 2 (2:1) to 540 (540:1), and is preferably between 2 to 25, particularly preferably in the region of 2.6 to 3.5 (for a 1:1 complex with cyclodextrin) or of 5.2 to 6.2 (for a 1:2 complex with cyclodextrin) for a molecular weight of the cyclodextrin of about 1,300.

It is preferred to prepare the complex from a concentrated, aqueous cyclodextrin preparation. The cyclodextrin concentration of the preparation is preferably between 50 and 400 mM. Preference is given to a cyclodextrin concentration of from 100 to 250 mM. Depending on the consistency, the mixtures are intensively stirred or kneaded. The percent by weight of the cyclodextrin is based upon the total weight of the aqueous cyclodextrin preparation.

It is further preferred to prepare the complex from a concentrated, aqueous cyclodextrin preparation in the presence of a L-lysine solution (L-lysine concentration between 10 mM and 1000 mM, preferably between 10 mM and 500 mM and more preferred between 10 mM and 100 mM). The cyclodextrin concentration of the preparation is preferably between 50 and 400 mM. Preference is given to a cyclodextrin concentration of from 100 to 250 mM. Depending on the consistency, the mixtures are intensively stirred or kneaded. The percent by weight of the cyclodextrin is based upon the total weight of the aqueous cyclodextrin preparation.

The reaction temperature is usually between 20° C. and 80° C., preferably between 20° C. and 60° C., particularly preferably between 25° C. and 45° C. The reaction time depends on the temperature and is at least some days. Preference is given to a reaction time of at least 7 days to reach equilibrium of complex formation. Subsequently, the reaction mixture is filtrated, if undissolved material is still present, or used directly, if completely dissolved. If desired, the complex can be isolated, e.g., by chromatographic means. Preferably, the concentrations and ratio of trioxopyrimidine and cyclodextrin are such that complex formation has occurred completely (reached the equilibrium) and no undissolved or uncomplexed trioxopyrimidine is detectable.

According to the invention it has been established that complexes between a trioxopyrimidine of formula I and a cyclodextrin increase the solubility of the trioxopyrimidine in water amazingly. It was also found that the formation of the complex did not interfere with the pharmacological properties of the trioxopyrimidine.

According to the invention it has been established that complexes between a trioxopyrimidine of formula I, a cyclodextrin and an adjuvant such L-lysine or L-arginine increase the solubility of the trioxopyrimidine in water amazingly. It was also found that the formation of the complex did not interfere with the pharmacological properties of the trioxopyrimidine.

All these properties allow to prepare liquid formulations as solutions for injection or for nebulization and allow the bioavailability to be improved, in particular orally. A trioxopyrimidine-cyclodextrin complex of the present invention may be used as such or in a powder form which is obtained by removing co-existing water. Examples of the method for removing water include lyophilization and drying under reduced pressure. A powder product obtained from lyophilization is particularly preferred.

The trioxopyrimidine-cyclodextrin complex of the present invention exhibits its effects through either oral administration or parenteral administration, and it is preferably formed into a formulation for parenteral administration, particularly an injection formulation or topical administration, particularly an aerosol formulation.

The dose of the complex of the present invention may be modified appropriately in accordance with the age, body weight, and severity of the patient's symptom and the complex may be administered at a single time or in a divided manner. Examples of the form of formulation include tablets, capsules, powders, and granules. These may be produced through a known technique by use of typical additives such as excipients, lubricants, and binders.

The invention relates to a method used for treating bronchial inflammatory diseases in a host mammal in need of such treatment, e.g., especially asthma and chronic obstructive pulmonary disease (COPD) by the application of a complex according to the invention to a patient in a pharmaceutically effective amount. Asthma is an inflammatory disease of the bronchial tree related or not to an allergen exposure. This inflammation provokes symptoms in patients by stimulating the bronchial smooth muscles to contract, enhancing the mucus secretion, and inducing bronchial morphological changes thought to be an aggravating factor regarding the course of the disease. Airway hyperresponsiveness is a hallmark of the disease and is responsible for most of symptoms. Bronchial tree is a very complex tissue with many cell types (epithelial cells, smooth muscle cells, inflammatory cells, nerves, mucus producing cells, fibroblasts, and the like) and the bronchial remodelling events which comprise many aspects mainly consist in a deposition of extracellular matrix components in the bronchial walls and an hyperplasia of the mucus producing cells. The use of complexes according to the invention inhibits the inflammatory cells influx in the compartments of bronchoalveolar lavage and peribronchial tissue and inhibits the hyperresponsiveness defined as an abnormal response to stimulating agents such as methacholine. The disease and current treatments are reviewed in e.g.: GINA Workshop Report, Global Strategy for Asthma Management and Prevention (NIH Publication No. 02-3659).

The invention therefore further relates to a method for treating or preventing in a host mammal in need of such treatment chronic obstructive pulmonary diseases using complexes according to the invention. In such a disease, bronchi are inflamed and the mucus glands are hyperplastic and produce high amounts of mucus. The bronchial wall is abnormal and deposition of abnormal extracellular matrix components increases the resistance to airflow. The disease and current treatments are described by, e.g., Fabbri, L. M., and Hurd, S. S., Eur. Respir. J. 22 (2003) 1-2.

The invention therefore further relates to a method for treating or preventing in a host mammal in need of such treatment emphysema using complexes according to the invention. In such a disease, the alveolar walls are destroyed by proteolytic processes and this destruction impairs the transfer of oxygen to the blood. Physiological problems also occurs because of the derived hyperinflation which causes abnormalities in the ventilation by causing a dysfunction of respiratory muscles and because of a hypertension in pulmonary arteries leading to cardiac failure in advanced stages.

According to the invention the trioxopyrimidine-cyclodextrin complexes are preferably administered over several months or years, to the patient in need of such a therapy. The complexes are administered preferably by the aerosolization of a liquid or powder formulation, with non toxic doses ranging between micro and nanomolar concentrations per kg and day.

The exact dosage of the complexes according to the invention will vary, but can be easily determined. In general, the daily dosage of the complexes will range between 1 µmol/kg and day to 100 nmol/kg and day (concentration of the trioxopyrimidine in the complex).

The pharmaceutical compositions are preferably aqueous compositions having physiological compatibility. The compositions include preferably, in addition, a pharmaceutically acceptable additive such as buffer, preservative and/or auxiliary substance. Appropriate buffer systems are based on sodium phosphate, sodium acetate or sodium borate. Preservatives are required to prevent microbial contamination of the pharmaceutical composition during use. Suitable preservatives are, for example, benzalkonium chloride, chlorobutanol, methylparabene, propylparabene, phenylethyl alcohol, sorbic acid. Such preservatives are used typically in an amount of 0.01 to 1% weight/volume.

Suitable auxiliary substances and pharmaceutical formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of a pharmaceutically acceptable substances include saline, Ringer's solution and dextrose solution. The pH of the solution is preferably from about 5 to about 8, and more preferably from about 7 to about 7.5.

If L-lysine or L-arginine are used as adjuvants for the complex formation, the pH of the solution is preferably from about 6 to about 8.5, and more preferably from about 7.5 to about 8.5.

A preferred formulation according to the invention is an injectable or nebulizable formulation, preferably prepared from CD and trioxopyrimidine in a molar ratio of 1 to 500.

The complex is prepared by dissolving CD in water, adding a trioxopyrimidine of formula I and heat in a water bath until the latter is completely dissolved. Preferably the solution is sterilized by filtration. Preferably the solution has a osmolality of 200-400, preferably about 300 mOs/kg. The pH is about 7.2. The concentration of trioxopyrimidine and/or of CD can be modified in function of the requirements. It is preferred to adjust the tonicity by addition of NaCl.

A preferred formulation for nebulization contains trioxopyrimidine, CD, NaCl and water. Especially preferred is a combination of (for 200 ml of solution): Trioxopyrimidine 0.05-0.2 g, preferably 0.1 g; 10-50 g CD, preferably 20 g CD, preferably HPβCD; sodium chloride 1.2-1.5 g, preferably 1.42 g (isotonicity) and water, preferably pyrogen-free, sterile, purified water ad 200 ml.

The solution was prepared by dissolving CD in 100 ml of purified water, adding trioxopyrimidine and NaCl by stirring so as to dissolve them and complete with water so as to obtain 200 ml of solution. Preferably the solution is sterilized by filtration through a 0.22 µm polypropylene membrane or by a steam sterilization process.

Other preferred formulations are ophthalmic use formulations, oral use formulations, intra-uterine devices. Associations with other systems can also be considered, like nano- or micropartides or liposomes for example.

The following examples, references, and figures are provided to aid the understanding of the present invention, the true scope of which is set forth in the appended claims. It is understood that modifications can be made in the procedures set forth without departing from the spirit of the invention.

ABBREVIATIONS

CD cyclodextrin
βCD β-cyclodextrin
γCD γ-cyclodextrin
DIMEβCD dimethyl β-cyclodextrin
HPβCD Hydroxypropyl β-cyclodextrin
RMβCD random methylated β-cyclodextrin
I.V. intravenous Example 1

Preparation of a Soluble Complex of Compound I and Cyclodextrin (CD)

1.1 Weigh 20 mg of compound I. Add 2 ml of solution of HPβCD 200 mM. Stir for 24 h at 37° C. Filter in Millipore filter Millex HV 0.45 μm. The solution obtained after filtration contains the complex compound I-CD in solution.

1.2. Weigh 2.5 mg of compound I. Add 2 ml of solution of HPβCD 200 mM. Stir at 37° C. for 24 h or until compound I is completely dissolved. The solution obtained in this way contains the complex compound I-CD.

Example 2

Phase Solubility Studies

Figure 1:
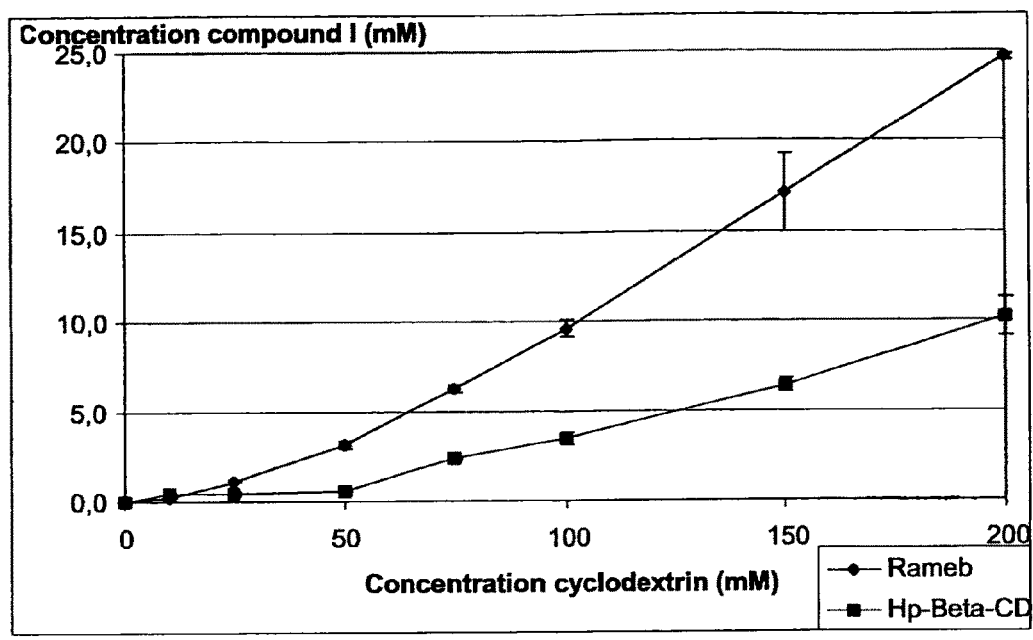
FIG. 1 shows the Compound I solubility obtained for both RMβCD and HP-β-CD. Phase solubility diagrams are both of $A_p$ type which means that CDs form complexes of stoechiometry 1:1 and 1:2. Stability constants were then calculated and their values are given in table 6.
Figure 2:
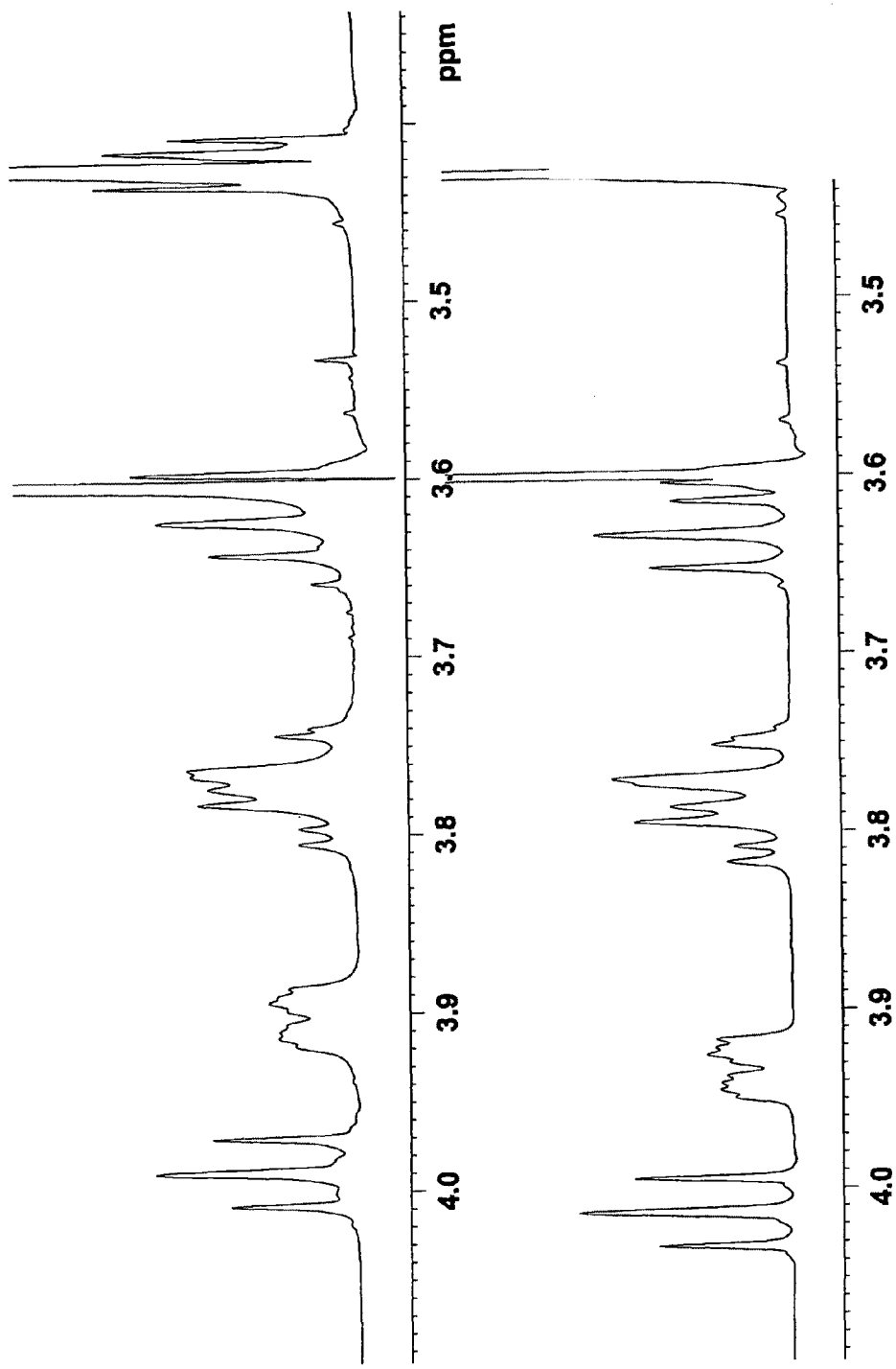
FIG. 2 NMR spectrum of the complex of Compound I and DIMEβCD (upper part) and of DIMEβCD alone (lower part).
Figure 3:
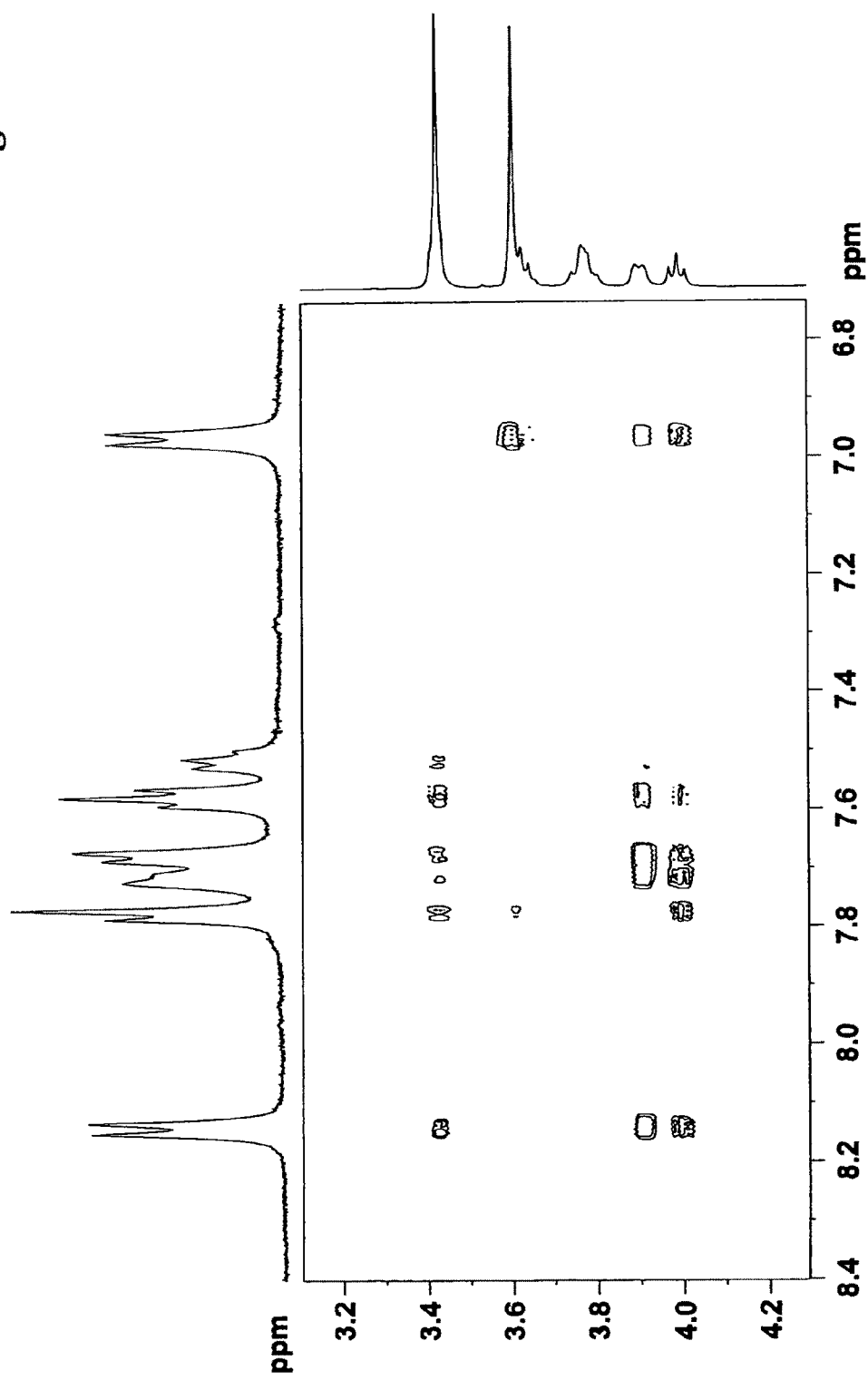
FIG. 3 NMR spectra of compound I (on the top), of DIMEβCD (on the right-hand side) and T-ROESY (in the middle).

At the time of a complex formation, compound I, practically insoluble in water (<0.6 μg/ml, MW: 485), solubilizes dramatically. The increase in the solubility of compound I is thus proof of a complex formation between Compound I and the CD. Complex formation and achievement of the equilibrium is found at 20% after 1 day, 40% after 4 days, and 100% after 7 days. The solubility diagrams (FIG. 1) are carried out by adding an excess of compound I to the CD solutions of increasing concentration. After 7 days of stirring in thermostatically controlled baths at 37° C., these solutions are filtered and the solubilized compound I quantity is dosed by HPLC. The βCD and the γCD as well as their synthetic derivatives have allowed complexes with compound I to be formed. The β-CD and the HPβCD come from ROQUETTE (France), the RMβCD and the γCD have been supplied by Wacker (Germany).

Preparation of CD Aqueous Solutions:
  βCD: Solutions containing 2, 4, 8, 10, 12, 16 mM.
  HPβCD: Solutions containing 10, 25, 50, 75, 100, 150, 200 mM.
  RMβCD: Solutions containing 10, 25, 50, 75, 100, 150, 200 mM.
  γCD: Solutions containing 10, 25, 50, 100, 75, 150 mM.

Complex Formation:
  The flasks containing compound I and the cyclodextrins are placed being stirred in thermostatically controlled baths at 37° C. for 7 days, so that the complexation balance is reached. After this time, the suspensions are filtered with the help of a milli-pore filter 0.22 μm in PVDF and the filtrate is dissolved in DMSO in the mobile phase to obtain concentration samples situating themselves on the calibrating line. They are then dosed thanks to the validated HPLC method, described below.

Dosage of Compound I: HPLC Method
Equipment:
  Pump Merck-Hitachi model L-7100, sampler Merck-Hitachi L-7200, furnace Merck-Hitachi L-7350, detector Merck-Hitachi Diode array detector L-7455, interface D-7000, the set being piloted by the data acquirement software "Chromatography Data Station Software" supplied by Merck-Hitachi.

Stationary Phase:
  Lichrocart Column (125×4 mm d.i.) filled with a stationary phase of octylsilane C8 LiChorspher® 60RP-Select B (5 μm) Merck.

Chromatographic Conditions:
  Mobile phase: mixture of phosphate buffer 0.05 M to pH=3 and methanol (30/70, v/v). Gas is extracted by an ultrasound passage for 15 minutes, output: 1 ml/min, λ of U.V. detection: 265 nm, Working temperature: 30° C., Injection volume: 20 μl.

The results of the HPLC dosages of Compound I are reproduced in the tables below (Tables 1 to 4) for each cyclodextrin. Without cyclodextrin, the solubility obtained is 0.56 μg/ml.

TABLE 1

Solubility of Compound I in the presence of HPβCD

| Concentration of CD in mM | Concentration of Compound I in μg/ml |
|---|---|
| 2 | 2.4 |
| 4 | 6.8 |
| 8 | 6.6 |
| 10 | 3.4 |
| 12 | 1.6 |
| 16 | 1.5 |

TABLE 2

Solubility of Compound I in the presence of HPβCD

| Concentration of CD in mM | Concentration of Compound I in μg/ml |
|---|---|
| 10 | 187.8 |
| 25 | 213.4 |
| 50 | 235.8 |
| 75 | 1129.3 |

TABLE 2-continued

Solubility of Compound I in the presence of HPβCD

| Concentration of CD in mM | Concentration of Compound I in µg/ml |
|---|---|
| 100 | 1664.6 |
| 150 | 3106.5 |
| 200 | 4962.1 |

TABLE 3

Solubility of Compound I in the presence of RMβCD

| Concentration in CD of mM | Concentration of Compound I in µg/ml |
|---|---|
| 10 | 120.6 |
| 25 | 526.7 |
| 50 | 1529.2 |
| 75 | 3012.4 |
| 100 | 4677.2 |
| 150 | 8317.6 |
| 200 | 11962.5 |

TABLE 4

Solubility of Compound I in the presence of γCD

| Concentration in CD of mM | Concentration in Compound I of µg/ml |
|---|---|
| 10 | 1.3 |
| 25 | 3.2 |
| 50 | 11.4 |
| 75 | 13.6 |
| 100 | 19.5 |
| 200 | 29.1 |

Compound I forms complexes with all the studied cyclodextrins because an increase in solubility is observed. It can also be directly observed that the complex formed between compound I and the Rameb increases the aqueous solubility of compound I considerably and completely unexpectedly. This observation is also true for the HP-β-CD. Table 5 summarizes the solubility results obtained for each cyclodextrin at the maximum concentration tested. The increase in solubility is calculated compared to the solubility of compound I in water (in the absence of cyclodextrin) which has been determined at 0.56 µg/ml.

Based on these results, phase-solubility diagrams were constructed according to Higuchi, T., and Connors, K. A., Advances in Analytical Chemistry and Instrumentation 4 (1965) 117-212.

TABLE 5

Maximum increase in solubility of Compound I obtained for each cyclodextrin

| | Maximum concentration used in mM for each CD | Maximum solubility in µg/ml | Increase in solubility |
|---|---|---|---|
| βCD | 4 | 6.8 | 12.1 |
| HPβCD | 200 | 4962 | 8860 x |
| RMβCD | 200 | 11926.5 | 21296 x |
| γCD | 200 | 29.1 | 51.96 x |

TABLE 6

| CD | Stoichiometry | $K_{1:1}[M^{-1}]$ | $K_{1:2}[M^{-1}]$ |
|---|---|---|---|
| βCD | 1:1; 1:2 | 2092 | — |
| γCD | 1:1 | 346 | — |
| HP-βCD | 1:1; 1:2 | 12575 | 14.4 |
| RMβCD | 1:1; 1:2 | 27595 | 22.88 |

The high values of $K_{1:1}$ suggest that, in purified water, the cavity of the β-CD derivatives accommodates very well the molecular portion of compound I involved in the inclusion. From 0 to 4 mM βCD concentration, the solubility of compound I increases and reaches a plateau up to 8 mM βCD. Concentrations of above 8 mM βCD form an additional complex of 1:2 stoichiometry (Cpd. I: βCD) with a lower solubility (1.5 µg/ml). The phase diagram obtained therefore is an $A_L$ diagram. For γ-CD, HP-βDC and RMβCD, an $A_p$ type diagram is obtained. The calculated stability constant of $346M^{-1}$ indicates that the cavity of the CD is too large to obtain sufficient interactions.

Compound I has different solubility when it is in the complex form or not. For example, compound I shows a good solubility in acetonitrile (±700 µg/ml) while the HP-β-CD and the compound I-CD complex is insoluble in this solvent. In these conditions the included drug remains trapped and becomes insoluble in the solvent. This technique of differential solubility between compound I in the free or in the complexed form can be applied to evaluate the percentage of complexation.

Example 3

Solubility of Various Trioxopyrimidines in the Presence of HPβCD

Solubility is investigated according to Examples 1 and 2. The results are shown in Table 7.

TABLE 7

| Concentration HPβCD [mM] | Concentration [mg/ml] | | | |
|---|---|---|---|---|
| | Compound III | Compound II | Compound IV | Compound V |
| 10 | 0.8 | 1.3 | 0.1 | 0.8 |
| 25 | 2.4 | 3.4 | 0.2 | 2.4 |
| 50 | 3.1 | 3.8 | 0.9 | 5.4 |
| 100 | 6.1 | 5.9 | 2.7 | 6.6 |
| 200 | 9.5 | 9.3 | 7.9 | 9.9 |

Example 4

Phase Solubility Studies with L-Lysine Solution as Adjuvant

Solubility studies were performed as described by Higuchi, T., and Connors, K. A., Advances in Analytical Chemistry and Instrumentation 4 (1965) 117-212. Excess amounts of Compound I were added to increasing concentrations of HP-β-CD (0-200 mM) in 5 ml dissolution media, either purified water or L-lysine solutions (50 mM or 500 mM). The glass containers were sealed and the suspensions were shaken in a water-bath at 25° C. until complexation equilibrium was reached (7 days). An aliquot was filtered through a 0.45 µm PVDF membrane filter and assayed for Compound I content by a validated liquid chromatography (LC) method.

Figure 7:
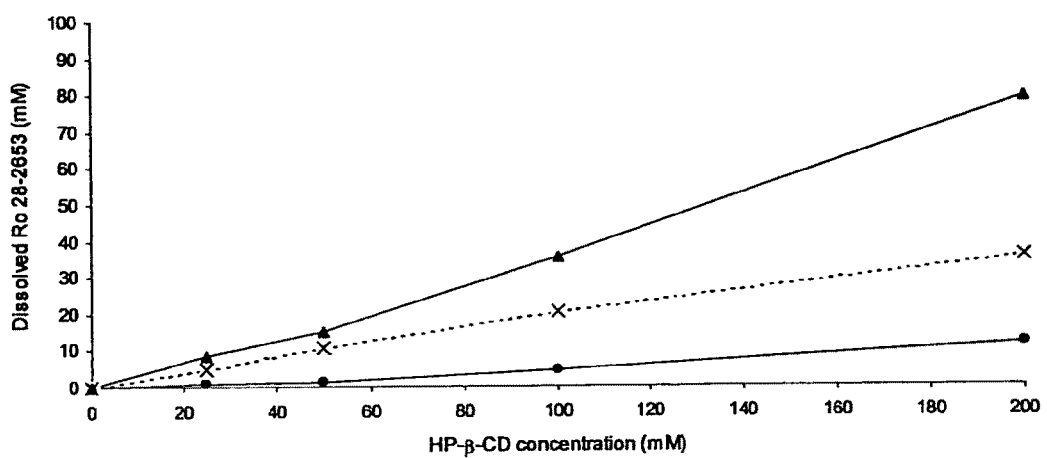
FIG. 7 Phase solubility diagram of Compound I with HP-β-CD in purified water (●), L-lysine 50 mM (x) or L-lysine 500 mM (▲).
Figure 8A:
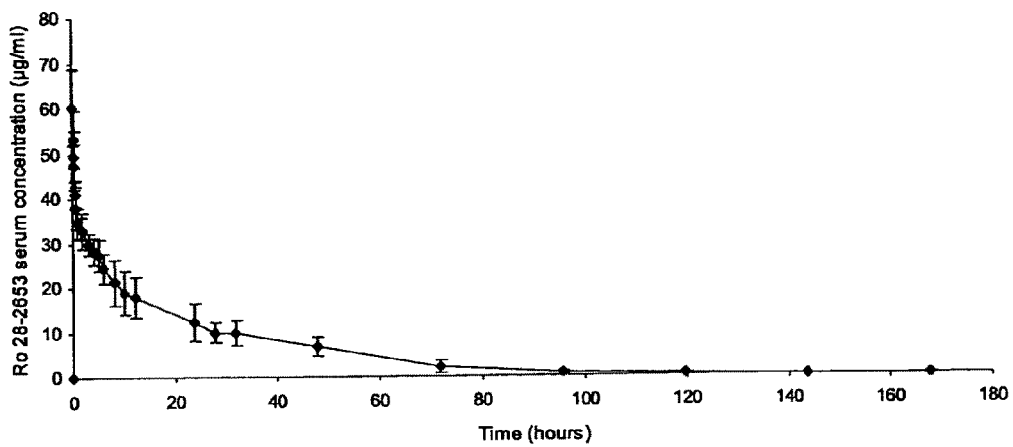
FIG. 8 Mean (±S.D.) Compound I serum concentration (a) or logarithm of the mean Compound I serum concentration (b) versus time curve after intravenous administration (5 mg/kg) to sheep (n=6).
Figure 8B:
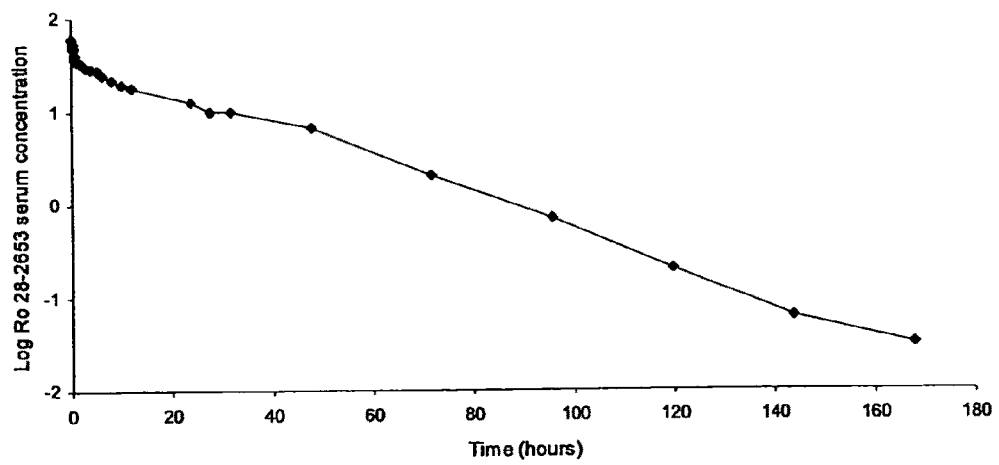

FIG. 7 shows the phase solubility diagram of Compound I obtained at 25° C. in the presence of HP-β-CD in purified water, in a 50 mM L-lysine solution and in a 500 mM L-lysine solution. In the three cases, the aqueous solubility of Compound I increases as a function of CD concentration. The solubility diagram obtained in the absence of L-lysine confirms the previously mentioned results: the solubility of Compound I in a 200 mM HP-β-CD solution is about 5.5 mg/ml (11 mM) which corresponds to an approximately 10,000-fold increase of the Compound I's aqueous solubility.

In the presence of L-lysine, the Compound I solubility in HP-β-CD solutions is even much higher. The solubility in a 200 mM HP-β-CD solution is increased about 2 and 7 times in the presence of 50 mM and 500 mM of L-lysine respectively. Table 8 shows solubility data of Compound I in the different media. Results show a synergistic effect between L-lysine and HP-β-CD. The solubility in the presence of both 500 mM L-lysine and 200 mM HP-β-CD (38.14 mg/ml) is higher than that expected by adding the effect of HP-β-CD and L-lysine separately (5.53 mg/ml and 0.09 mg/ml). This synergistic effect between L-lysine and HP-β-CD allows an important increase of Compound I aqueous solubility (70,000-fold with 500 mM of L-lysine and 200 mM of HP-β-CD).

TABLE 8

Solubility of Compound I [mg/ml] in purified water and in L-lysine (50 mM and 500 mM) without or with HP-β-CD (200 mM)

|   | Solubility without CD [µg/ml] | Solubility with HP-β-CD (200 mM) [µg/ml] |
|---|---|---|
| Purified Water | 0.56 | 5530 |
| L-lysine 50 mM | 50 | 17080 |
| L-lysine 500 mM | 90 | 38140 |

Example 5

NMR Studies

DIME-β-CD solutions were prepared in D$_2$O at 10 mM concentration. As water solubility of compound I is too low, spectra of compound I alone could not be performed in D$_2$O. For assignment of the protons, NMR spectra of compound I were performed in DMSO. All NMR experiments were performed on a Bruker DRX500 spectrometer operating at 500 MHz for proton. The temperature was set to 298K. Calibration was achieved using the residual resonance of the solvent as secondary reference of HDO. For T-ROESY experiments, a 300 msec mixing time was used. All processing were done on Silicon Graphics INDY data stations using WINNMR program for Bruker. The comparison between compound I NMR spectra alone and in presence of an excess of DIME-βCD allows to notice that the signals corresponding to H-3 and H-5 protons are shifted up field. This shift constitutes a proof of the inclusion. The T-ROESY spectra analysis demonstrates the inclusion of compound I in the CD cavity. Two different parts of the molecule can fit into CDs cavity.

Example 6

Molecular Modeling Studies

Molecular modeling calculations have been performed with Gaussian 94 using the POBRON crystallographic structure of β-CD Of the Cambridge Data Base. Two extreme spatial conformations of compound I were calculated. The results obtained show the inclusion is energetically feasible and very stable. This stability can be explained by the formation of hydrogen bounds between the oxygen and the proton of the nitrogen of the barbituric nucleus and the alcohols situated at the outside of the CD. All the pharmaceutical compositions including compound I and a cyclodextrin (preferably βCD, γCD and their synthetic derivatives) either in complexes form, or in association, are anticipated in the framework of the invention, whatever their form and their therapeutic application. In fact, even if compound I and the CDs are not in the form of complex in the formulation, this one is susceptible to be formed in situ.

Example 7

Pharmaceutical Compositions

Different compositions of formulations are given for example non-exhaustively.
A preferred example for an injectable formulation is:
HP-βCD 200 mM; Compound I I mg/ml; Sterile water for injection q.s.
For 25 ml of solution:
a) Preparation of the Solution:
  Weigh 6.77 g of HPβCD (4.2% of H$_2$O) and dissolve them in 25 ml of water by injection. Add 25 mg of compound I and heat in a water bath until the latter is completely dissolved. Sterilize the solution by filtration.
b) Characteristics of the Solution:
  The solution osmolality is 308 mOs/kg. The pH is 7.2.
  The concentration of compound I and/or of CD can be modified in function of the requirements. It is preferred to adjust the tonicity by addition of NaCl.
A preferred formulation for nebulization is:
For 200 ml of solution:

| Compound I | 0.1 g (MW: 485) |
| HPβCD exempt from pyrogenic | 20.15 g (MW: 1,300) |
| Sodium chloride | 1.42 g (isotonicity) |
| Pyrogen-free, sterile, purified water, | q.s. ad 200 ml | a) Weigh 20.15 g of HPβCD exempt from pyrogenic (3.2% H$_2$O, ROQUETTE) and dissolve them in 100 ml of purified water.
b) Weigh 0.1 g of compound I, and 1.42 g of sodium chloride and add them to solution (a) by energetically stirring so as to dissolve them.
c) Complete with water so as to obtain 200 ml of solution.
d) Sterilize by filtration through a 0.22 µm polypropylene membrane.

Example 8

Pharmacokinetic Studies on the Bioavailability

Solutions for the pharmacokinetic studies were developed with a combination of HP-β-CD and L-lysine allowing a high Compound I concentration with a biocompatible pH value.
Dosage Form Preparations
The Compound I/HP-β-CD intravenous solution was obtained by dissolving Compound I (10 mg/ml) in a solution containing HP-β-CD (200 mM), L-lysine (20 mM) and water for injection. The osmolality (about 325 mOsmol/kg) and the pH (about 8.2) values of this solution are compatible with an intravenous injection. The solution was sterilized by passing through a sterile 0.20 μm cellulose acetate filter under aseptic conditions.

The Compound I/HP-β-CD oral solution was prepared by dissolving Compound I (15 mg/ml) in a solution containing HP-β-CD (200 mM), L-lysine (50 mM) and water.

The Compound I suspension was composed of Compound I (15 mg/ml), polysorbate 80 (0.1 mg/ml) as wetting agent, simaldrate (VEEGUM HV®, 1% m/v) and methylcellulose (METHOCEL A400®, 0.4% m/v) as viscosifying agents.

Animal Experimental Protocol and Drug Administration

Six healthy sheep (2 males and 4 females) ranging from 45 to 82 kg of body weight were used as experimental animals. During the test, the animals were fed and watered ad libitum.

The experimental study, which was realized following the scheme of Table 9, included a randomized two-way crossover design for oral administration followed by an intravenous administration. A wash-out period of 3 weeks was allowed between each administration.

TABLE 9

Animal experimental design for administration of solutions and suspension containing Compound I

| Sheep | $1^{st}$ phase | $2^{nd}$ phase | $3^{rd}$ phase |
|---|---|---|---|
| 1 | Oral suspension | Oral solution | I.V. solution |
| 2 | Oral suspension | Oral solution | I.V. solution |
| 3 | Oral suspension | Oral solution | I.V. solution |
| 4 | Oral solution | Oral suspension | I.V. solution |
| 5 | Oral solution | Oral suspension | I.V. solution |
| 6 | Oral solution | Oral suspension | I.V. solution |

For the oral dosage forms, each animal received a Compound I dose equal to 15 mg/kg of body weight from both formulations. Sheep were weighed on the day of drug administration in order to adapt the dosage form volume. Blood samples were taken from jugular vein before and 0.25, 0.5, 1, 1.5, 2, 3, 4, 6, 8, 10, 12, 24, 28, 32, 48, 72, 96, 120, 144, 168 hours after oral administration.

For the intravenous dosage form, all six sheep received 5 mg of Compound I/kg of body weight. The solution was administered through the left jugular vein and blood samples were taken from the right jugular vein before and 5, 10, 15, 20, 30, 45 min, 1, 1.5, 2, 3, 4, 5, 6, 8, 10, 12, 24, 28, 32, 48, 72, 96, 120, 144, 168 h after starting the intravenous administration.

All blood samples were centrifuged and the serum were stored at −80° C. until assayed.

Bioanalysis Method

A fully automated method was developed for the LC determination of this compound in serum. Sample clean-up was performed by on-line coupling of a pre-column packed with restricted access material (RAM), namely LiChrospher RP-8 ADS (alkyl diol silica), to the analytical column by means of the column-switching technique. The ADS sorbents belong to the group of internal surface reversed-phase supports and have been applied successfully for the dean-up of biological samples prior to LC analysis (Yu, Z., and Westerlund, D., Chromatographia 44 (1997) 589-594; Hubert, Ph., et al, S. T. P. Pharma Pratiques 9 (1999) 160-180; Souverain, S., et al., Journal of Chromatography B 801 (2004) 141-156). The operating conditions are described in a previous paper (Chiap, P., et al., Journal of Chromatography B 817 (2005), 109-117). The method was fully validated according to a novel approach based on accuracy profiles taking into account the total measurement error (Hubert, P., et al., Analytica Chimica Acta 391 (1999) 135-148; Hubert, Ph., et al., S. T. P. Pharma Pratiques 13 (2003) 27-64; Hubert, Ph., et al., J. Pharm. Biomed. Anal. 36 (2004) 579-586).

For the bioanalytical study, the dosing range of the method had to be increased until 50 μg/ml due to high concentrations to be determined. A partial revalidation was performed and good results were obtained with respect to response function, trueness, precision, accuracy and linearity.

Pharmacokinetics and Statistical Analysis

For the intravenous administration study, the pharmacokinetic parameters were determined for each animal using a linear two-compartment model with first-order distribution and elimination (Boroujerdi, M., Pharmacokinetics, Principles and Applications. McGraw-Hill Companies, USA, 2002). The areas under the curve values ($AUCs_{0-168}$) were calculated by linear trapezoidal rule during the sampling period. The AUC extrapolated until infinite values ($AUCs_{0-\infty}$) the total body clearance values ($Cl_t$), the biologic half-life ($T_{1/2\beta}$) and the overall volume of distribution ($Vd_t$) were calculated using conventional equations associated with compartmental analysis (Boroujerdi, M., Pharmacokinetics, Principles and Applications. McGraw-Hill Companies, USA, 2002).

For the oral administration study, the pharmacokinetic parameters were determined, for each animal and for both suspension and solution, using a linear one-compartment model with first-order input and first-order output (Boroujerdi, M., Pharmacokinetics, Principles and Applications. McGraw-Hill Companies, USA, 2002). The $AUCs_{0-168}$ were calculated as described above by trapezoidal summation. The $AUCs_{0-\infty}$ were estimated by the following equation (equation 1):

$$AUC_{0-\infty} = C_0 \left( \frac{1}{K} - \frac{1}{k_a} \right) \qquad \text{Equation 1}$$

where K and $k_a$ are respectively overall elimination rate constant and absorption rate constant and $C_o$ is the extrapolated concentration at the origin.

The maximum concentrations of drug in plasma ($C_{max}$) and the corresponding times ($T_{max}$) were determined for each animal by two different means: directly from the concentration-time graphs ($C_{max\ experimental}$ and $T_{max\ experimental}$) and calculated using the following equations (equation 2 and 3) ($C_{max\ calculated}$ and $T_{max\ calculated}$):

$$C_{max\ calculated} = C_0(e^{-KT_{max}} - e^{-k_aT_{max}}) \qquad \text{Equation 2}$$

$$T_{max\ calculated} = \frac{2.303}{k_a - K} \log \frac{k_a}{K} \qquad \text{Equation 3}$$

Absolute bioavailability ($F_{absol}$) was evaluated using the following relation (equation 4):

$$F_{absol} = \frac{AUC_{oral} \cdot D_{IV}}{AUC_{IV} \cdot D_{oral}} \qquad \text{Equation 4}$$

where $D_{oral}$ and $D_{I.V.}$ are the oral and I.V. administered drug quantities respectively.

All pharmacokinetic parameters are reported as means±standard deviations except absolute bioavailability, calculated from average $AUC_{0-\infty}$.

Data were regarded as aberrant when the individual AUC value was higher or lower than mean±2 standard deviations. Based on this, one sheep was excluded from the pharmacokinetic parameters determination after the oral solution administration and for statistical analysis.

The comparison of pharmacokinetic parameters for the two oral dosage forms has been performed with a two-way analysis of variance (two-way ANOVA). After log-transformation in order to normalize the distribution, the mean values of each calculated parameter were compared. Results were considered to be significant at the 5% critical level (p<0.05).

Pharmacokinetics of Compound I after Intravenous Administration

Figure 9A:
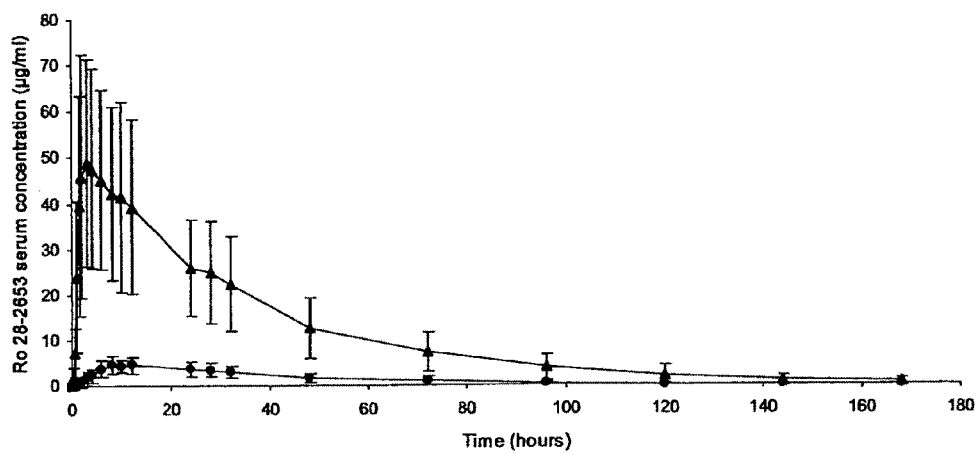
FIG. 9 Mean (±S.D.) Compound I serum concentration (a) or logarithm of the mean Compound I serum concentration (b) versus time curve after oral administration (15 mg/kg) of a solution (▲) and a suspension (●) to sheep (n=5 for solution and n=6 for suspension).
Figure 9B:
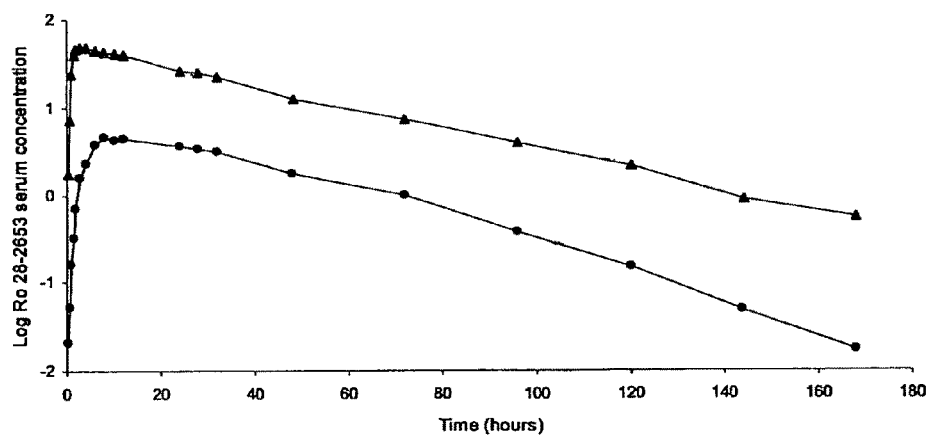

The mean Compound I serum concentration versus time curve obtained after a single administration of the intravenous solution (5 mg/kg) to sheep is reported in FIG. 9a. FIG. 9b (logarithm of the mean Compound I serum concentration versus time curve) shows that the Compound I pharmacokinetics follow a two-compartment model. The different pharmacokinetic parameters calculated after this intravenous administration are listed in Table 10.

TABLE 10

Compound I pharmacokinetic parameters (mean ± S.D.) obtained after intravenous administration (5 mg/kg) to sheep (n = 6)

|  | I.V. Solution |
|---|---|
| $AUC_{0-168\,h}$ (µg · h/ml) | 858.11 ± 211.58 |
| $AUC_{0-\infty}$ (µg · h/ml) | 858.87 ± 212.08 |
| $Cl_t$ (ml/h) | 358.76 ± 67.47 |
| $Vd_t$ (l) | 8.18 ± 2.16 |
| $T_{1/2\beta}$ (h) | 15.76 ± 2.34 |

The distribution phase is short (about 30 minutes) showing that Compound I is rapidly distributed in the organism. The overall volume of distribution is small (about 8 liters) which indicates that Compound I distribution would be limited to extracellular fluids and that Compound I diffusion into tissues would not be very important. On the other hand, the Compound I biologic half-life is long (about 15.5 h) and, so, drug elimination is very slow. Considering its small distribution volume, the accumulation in the organism would not be caused by storage for example in fat but maybe by a strong binding with proteins or other components of plasma. The total body clearance value was also calculated and is around 358.5 ml/h.

Pharmacokinetics of Compound I after Oral Administration of a Suspension and a Solution The mean serum concentration versus time profiles of Compound I obtained after oral administration of a single dose (15 mg/kg) of Compound I solution and suspension are shown in FIG. 10a. After logarithmic transformation of mean serum concentration, it seems that the pharmacokinetics after oral administration would follow a one-compartment model (FIG. 10b). The pharmacokinetic parameters are summarized in Table 11.

TABLE 11

Compound I pharmacokinetic parameters (mean ± S.D., except for F) obtained after oral administration (15 mg/kg) to sheep

|  | Oral Solution (n = 5) | Suspension (n = 6) | p-value (n = 5) |
|---|---|---|---|
| $AUC_{0-168\,h}$ (µg · h/ml) | 1848.66 ± 854.97 | 208.94 ± 103.82 |  |
| $AUC_{0-\infty}$ (µg · h/ml) | 2070.13 ± 943.79 | 214.65 ± 103.04 | 0.0035 |
| $C_{max\ experimental}$ (µg/ml) | 51.84 ± 23.73 | 4.84 ± 1.95 | 0.0009 |
| $C_{max\ calculated}$ (µg/ml) | 56.85 ± 24.67 | 5.34 ± 2.24 | 0.0010 |
| $T_{max\ experimental}$ (h) | 3.59 ± 1.52 | 12.34 ± 5.99 | 0.0094 |
| $T_{max\ calculated}$ (h) | 3.98 ± 0.57 | 10.42 ± 3.01 | 0.0046 |
| $F_{absol}$ | 0.80 | 0.08 |  |

The serum concentrations of Compound I after administration of the solution are clearly higher than those obtained with an equal dose administered as a suspension. The absorption phase observed with the solution (about 4 h) is shorter than that achieved after administration of the suspension (about 10 h). It can also be seen significantly different (p<0.05) (Table 11). The mean Compound I serum peak concentrations are about 54 and 5 µg/ml after administration of the solution and the suspension respectively. $C_{max}$ of the solution is about 10 times higher than that of the suspension. A three times earlier $T_{max}$ is obtained with the solution (about 3.8 h) than with the suspension (about 11 h). The AUC values follow the same trend as do the $C_{max}$ values: the AUCs after administration of the solution are about 10-fold higher than those after administration of the suspension. Consequently, after comparison with the I.V. solution, the absolute bioavailability is much higher with the solution (80%) than with the suspension (8%).

Example 9

In Vivo Experiments

Inhibition of Angiogenesis

In order to study the potential effects of the complex Compound I-cyclodextrine, a model of neovascularisation has been used. An aorta ring is cut and placed in a culture medium. This culture medium containing either:
- no active principle
- the complex compound I-cyclodextrins (final concentration $10^{-6}$M, $10^{-7}$M)
- compound I dissolved in DMSO with the help of DMSO (final concentration $10^{-6}$, $10^{-7}$M).

In the absence of the matrix metalloproteinase inhibitor compound I, the formation of new vessels (angiogenesis) is observed. In the presence of compound I alone, dissolved in DMSO, or in the form of inclusion complex in cyclodextrin, angiogenesis is inhibited significantly.

Example 10

Use of Formulations Containing Compound I and HPβCD for Therapy of Allergen-Induced Airway Inflammation and Bronchial Hyperresponsiveness in a Mouse Model of Asthma Materials HP-β-CD (degree of substitution=0.64) originates from Roquette (France). Apyrogenic phosphate buffered saline (PBS) was purchased from Bio-Wittaker (Verviers, Belgium) and methacholine from Sigma-Aldrich (Germany). All other materials were of analytical grade. Sterile water for injection was used throughout this study. Sterile, apyrogenic and isotonic CD solutions were prepared at 20, 50 and 75 mM. A commercially available fluticasone solution for inhalation (Flixotid® 1 mg/ml) was purchased from Glaxo-Smithkline (Genval, Belgium)

Sensitization, Allergen Exposure and Therapeutic Protocols

In order to study the modulation of airway inflammation by intraperitoneal injection of Compound I, mice were sensitized with 10 μg ovalbumin alumin-adsorbed (aluminject, perbio, Erembodegem, Belgium) injected intraperitonealy at days 0 and 7 and were subsequently exposed to ovalbumin (OVA) 1% or PBS aerosols for 30 minutes from day 21 to 24. Intraperitoneal injections were performed 30 min before OVA inhalations. The different injected formulations were: cremophor 10%-DMSO 10%-PBS 80%-Compound I 30 mg/kg (suspension); cremophor 10%-DMSO 10%-PBS 80%-Compound I 3.75 mg/kg (solution); HPβCD 200 mM Compound I 7.5 mg/kg (solution); HPβCD 200 mM. All results were compared to mice sensitized with OVA and exposed to PBS and OVA treated with PBS injected intraperitonealy. In order to study the modulation of airway inflammation by inhaled Compound I, mice were sensitized as described previously. Two protocols referred to as short exposure challenge and long-term exposure challenge were used. In the short exposure challenge, mice were exposed to aerosols of Compound I-complex at concentrations of 0.03 and 0.3 mg/ml of active compound in aqueous solution of from day 21 to 27 during 30 min in a Plexiglas exposure chamber (30×20×15 cm). Mice were exposed to OVA aerosols 30 minutes after the Compound I inhalation from day 23 to 27. In the so called long-term inhalation challenge, mice were exposed to aerosols of Compound I at concentrations of 0.03 and 0.3 mg/ml complexed with HPβCD in an aqueous solution during 30 min five clays odd weeks and to OVA aerosols 3 days odd weeks for 11 weeks. No inhalations were performed during even weeks.

The aerosol were produced by using an ultrasonic nebuliser SYSTAM (Système Assistance Medical, Le Ledat, France), the vibration frequency of which is 2.4 MHz with variable vibration intensity and ventilation levels. Vibration intensity was fixed in position 6 and the ventilation level was 25($v_{1/2}$) l/min.

Airway Responsiveness Measurement

Twenty-four hours after the last allergen exposure, the bronchial hyper responsiveness was determined by measuring the Penh using a barometric plethysmograph as proposed by Hamelmann, E., et al., Am. J. Respir. Grit. Care Med. 156 (1997) 766-775). The Penh was measured at baseline and 5 min after the inhalation of increasing doses (25, 50, 75 and 100 mM) of methacholine (Mch).

Bronchoalveolar Lavage (BAL) and Histology

Immediately after the assessment of airway responsiveness, mice were sacrificed and 1 ml of PBS free of ionised calcium and magnesium but supplemented with 0.05 mM sodium EDTA was instilled 4 times via a tracheal cannula and recovered by gentle manual aspiration. The recovered bronchoalveolar lavage fluid (BAL) was centrifuged (1800 rpm for 10 min at 4° C.). The cell pellet was washed twice and finally resuspended in 1 ml of PBS. A total cell count was performed in a Thoma chamber and the differential cell counts on at least 400 cells were performed on cytocentrifuged preparations (Cytospin 2; Cytospin, Shandon td., Runcorn, Cheshire, U.K.) using standard morphologic criteria after staining with Diff-Quick (Dade, Germany). After BAL, the thorax was opened and the left main bronchus was clamped. The left lung was excised and frozen immediately in liquid $N_2$ for protein chemistry and mRNA extraction while the right lung was processed for histology. As previously described (Cataldo, D. D., et al, Am. J. Pathol. 161 (2002) 491-498), the right lung was infused with 4% paraformaldehyde and embedded in paraffin. Sections of 5 μm thickness from all lobes were stained with haematoxylin and eosin. The extent of peribronchial infiltrates was estimated by an inflammation score. Slides were coded and the peribronchial inflammation was graded in a blinded fashion using a reproducible scoring system described elsewhere (Cataldo, D. D., et al., Am. J. Pathol. 161 (2002) 491-498). A value from 0 to 3 per criteria was adjudged to each tissue section scored. A value of 0 was adjudged when no inflammation was detectable, a value of 1 for occasional cuffing with inflammatory cells, a value of 2 when most bronchi were surrounded by a thin layer (1 to 5 cells) of inflammatory cells and a value of 3 when most bronchi were surrounded by a thick layer (>5 cells) of inflammatory cells. As 5-7 randomly selected tissue sections per mouse were scored, inflammation scores could be expressed as a mean value per animal and could be compared between groups. Another score referred to as tissue eosinophil infiltration score, specifically reflecting the amounts of eosinophils infiltrating the bronchial walls, was measured as follows: after a congo red staining, seven bronchi were studied per mouse. The eosinophils were counted around the bronchi within the limits of the airway wall, the perimeter of the epithelial basement membrane was measured and the results were expressed as number of eosinophils/mm of basement membrane. The left lung was snap frozen in liquid nitrogen and crushed using a Mikro-Dismembrator S (Braun Biotech International, Melsungen, Germany) and the extracts stored at −80° C. before studied. Kidneys were excised and paraffin embedded, sections of 5 μm were stained by haematoxylin and eosin. Blood was sampled by cardiac puncture and serum was stored at −80° C. until analysis were performed.

All in vivo manipulations were approved by the local Veterinarian Ethics Committee.

Intraperitoneal Injection of Compound I

Figure 4A:
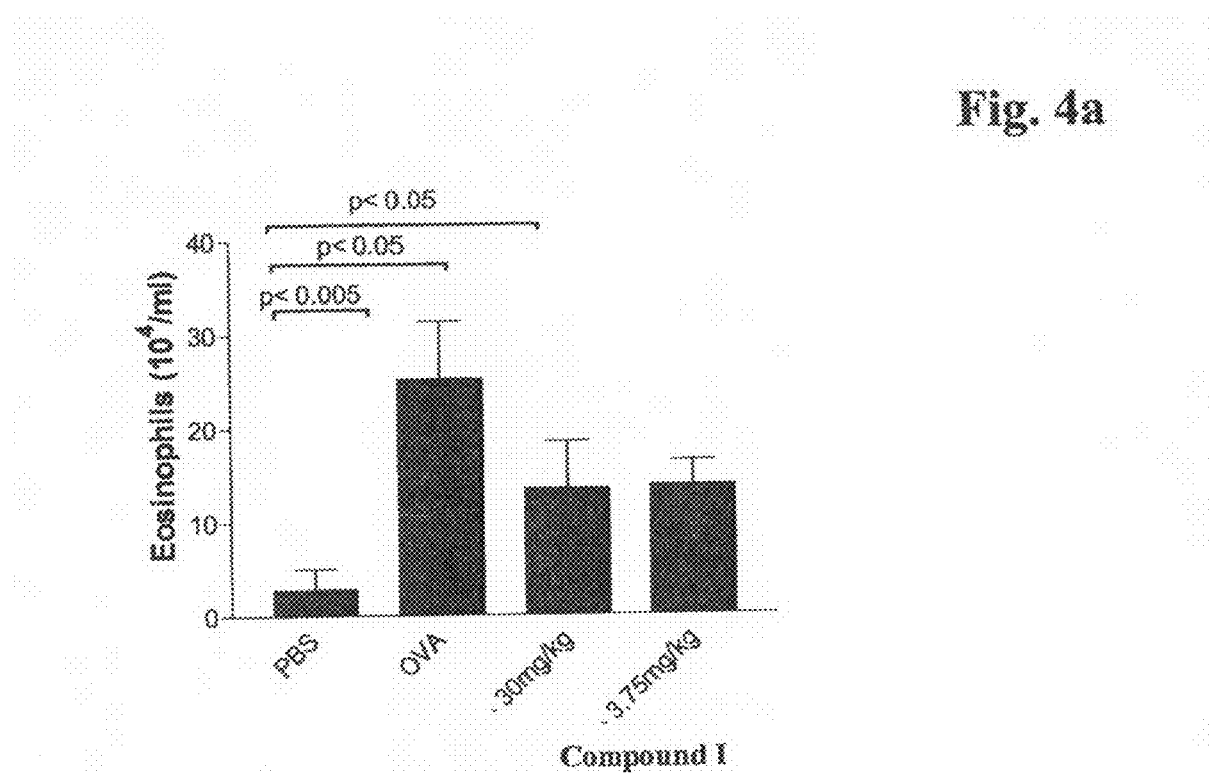
FIG. 4 Effects of intraperitoneal injection of a Compound I suspension on BAL eosinophil counts (FIG. 4a) and peribronchial inflammation score (FIG. 4b). Controls are mice exposed only to PBS and not allergen (PBS) and mice exposed to ova by inhalation and placebo by intraperitoneal injection (OVA).
Figure 4B:
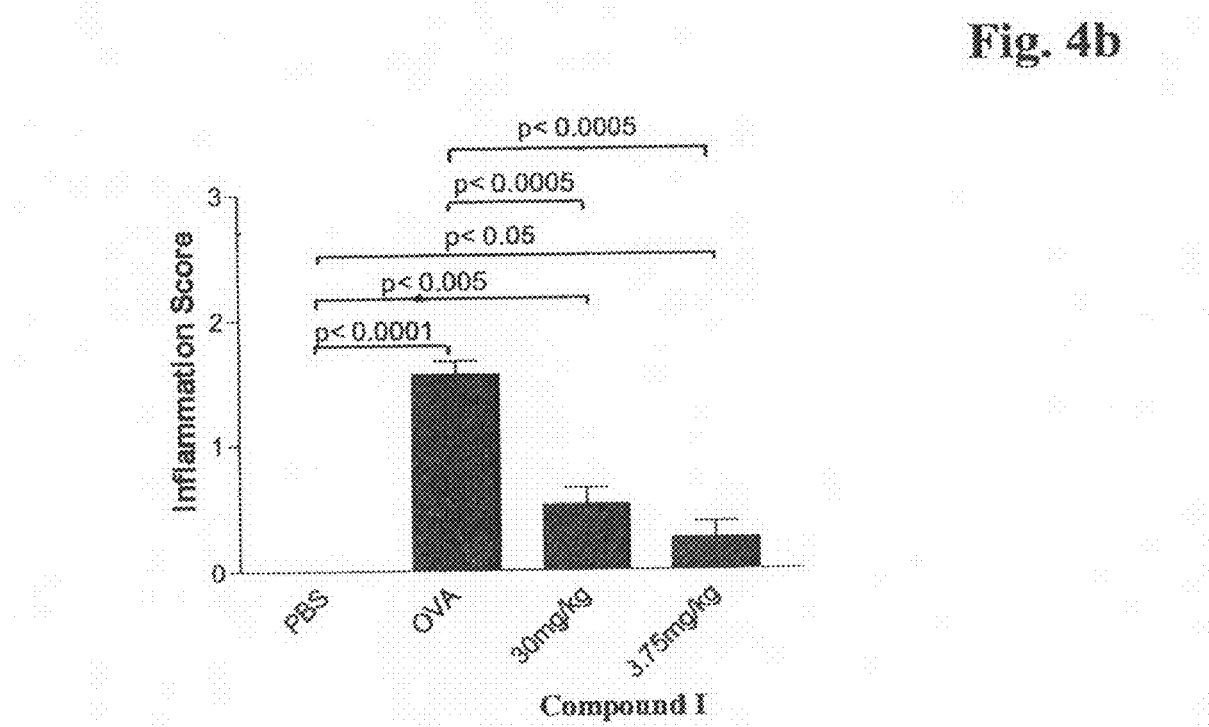

The intraperitoneal injection of Compound I (either solution or precipitate) lowered the allergen-induced airway eosinophilic inflammation in BAL at doses of 3.75 to 30 mg/kg when compared to placebo (FIG. 4a). At the same doses, the peribronchial inflammation scores were also significantly lowered by Compound I with an equal efficacy of all tested formulations (FIG. 4b). The tissue eosinophil infiltration score was significantly lowered by the intraperitoneal injection of Compound I at doses of 7.5 and 25 mg/kg.

Inhalational Exposure to Compound I and Compound I-HPβCD Complexes

The intrinsic activity of Compound I was firstly assessed as a topically active anti-inflammatory agent by using a solution of Compound I 40 mg/ml in pure DMSO in a short-term exposure. When compared to the inhalation of DMSO alone, the inhalation of this formulation led to a significant decrease of BAL eosinophils ($p<0.005$), peribronchial inflammation scores ($p<0.01$), as well as bronchial hyperresponsiveness ($p<0.05$).

Figure 5A:
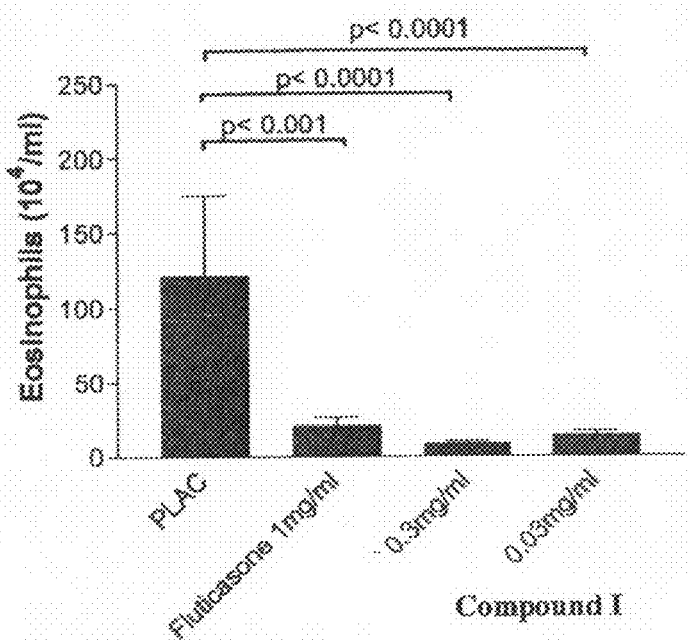
FIG. 5 Therapeutic effects of Compound I-HP-β-CD complex, fluticasone and placebo (PLAC) administered by aerosols on BAL eosinophilia (5a), peribronchial inflammation score (5b), and tissue eosinophils infiltration score (5c) in a short term (5 days) allergen exposure model.
Figure 5B:
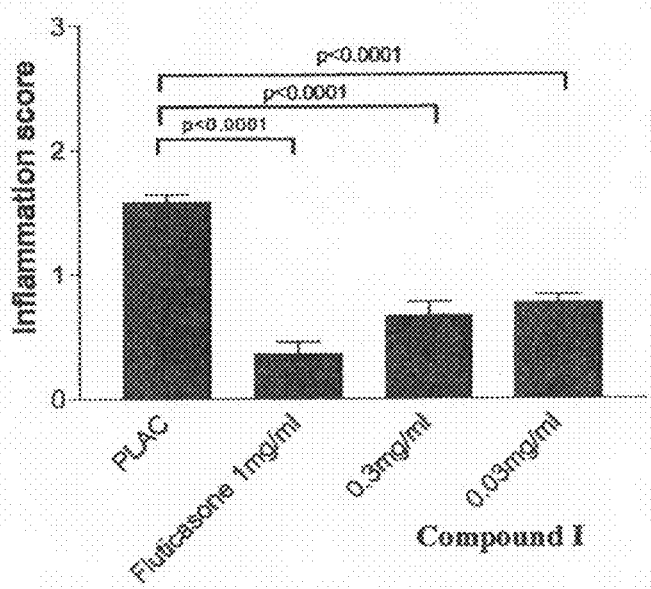
Figure 5C:
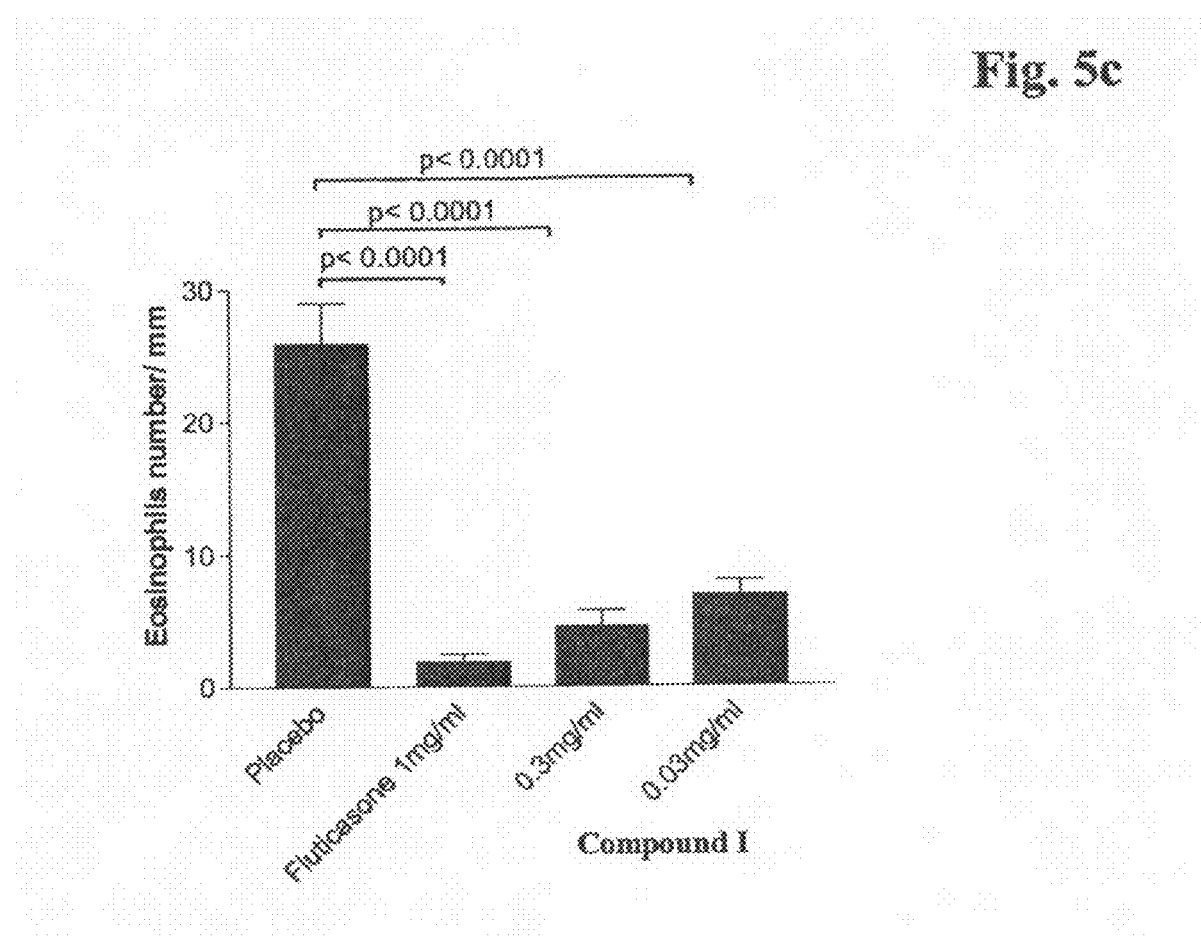

In the short-term exposure protocol, we assessed the effects of HP-β-CD Compound I complexes containing formulations on the airway inflammation and hyperresponsiveness. The effects of inhalation of Compound I-HPβCD complex containing formulations were compared with those of placebo (PBS) or fluticasone (1 mg/ml) used as reference therapy. Inhalation of those formulations containing Compound I at doses of 0.03 and 0.3 mg/ml induced a significant decrease in eosinophilic inflammation in BAL in an extent comparable to that of fluticasone when compared to placebo ($p<0.0001$) (FIG. 5a). Peribronchial inflammation scores were also lowered when compared to placebo (p<0.0001) (FIG. 5b), as well as the tissue eosinophil infiltration score (p<0.01) (FIG. 5c).

Figure 6A:
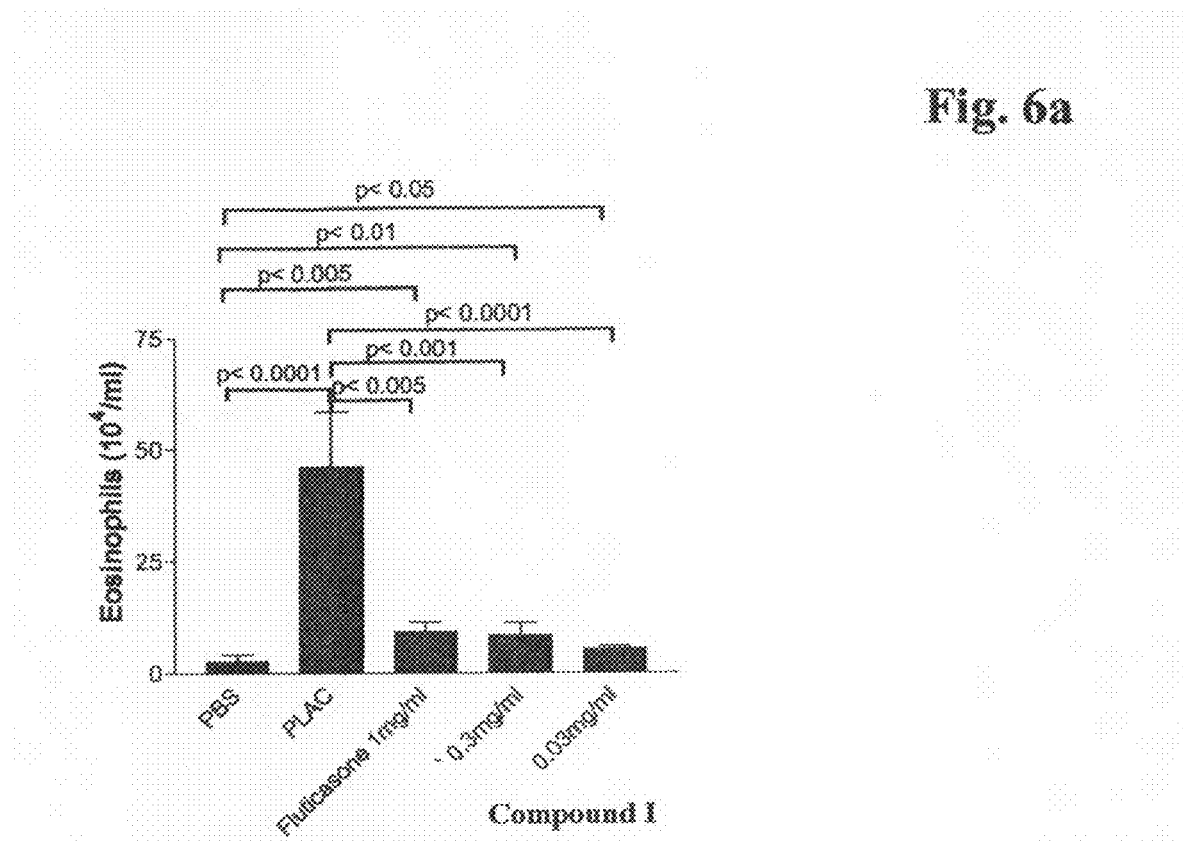
FIG. 6 Therapeutic effects of Compound I-HP-□-CD complex, fluticasone and placebo (PBS) administered by aerosols on BAL eosinophilia (6a), peribronchial inflammation score (6b), and tissue eosinophils infiltration score (6c) in a long term (11 weeks) allergen exposure model. Mice sensitized but unexposed to allergens (PBS) and mice sensitized and exposed to OVA (PLAC) were treated by PBS inhalation.
Figure 6B:
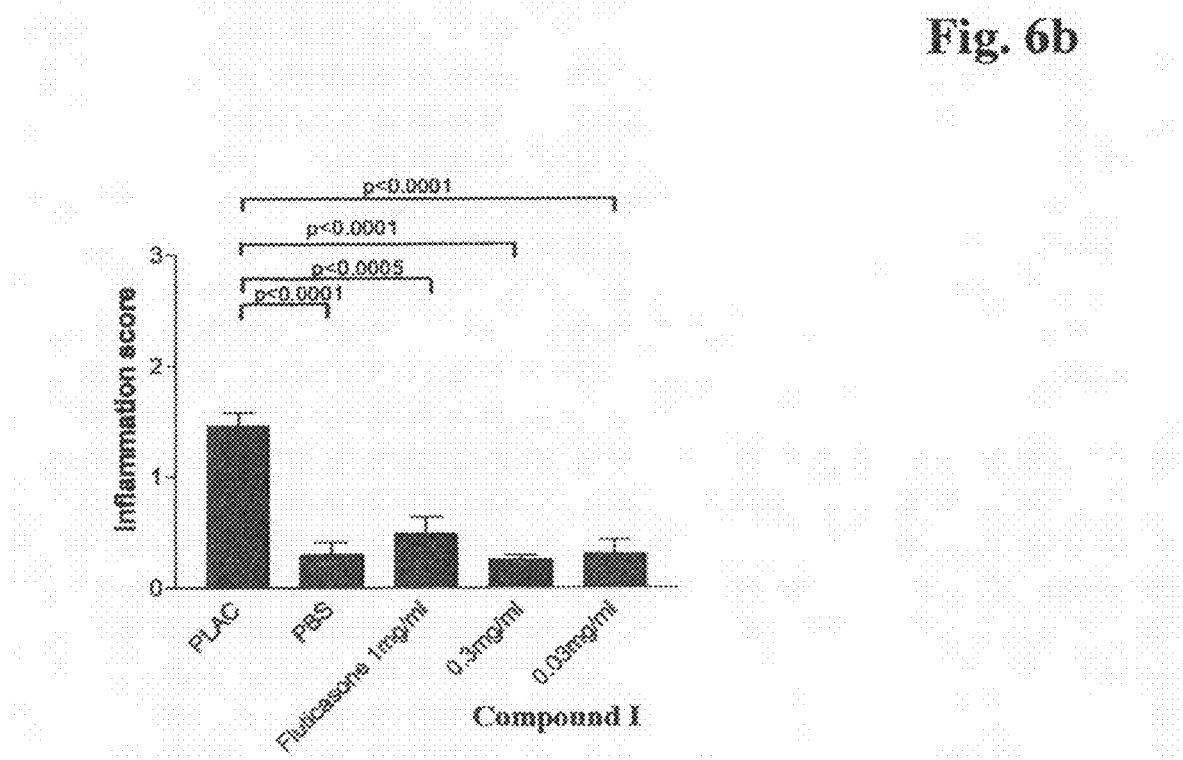
Figure 6C:
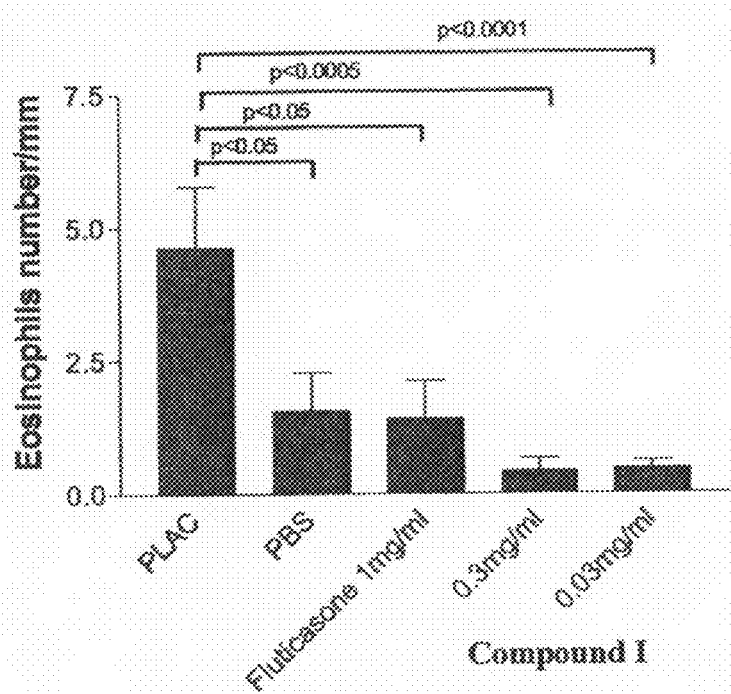

After long term allergen exposure, BAL eosinophilia was significantly decreased after treatment by inhalation of Compound I-HPβCD containing formulations (p<0.001) in the same extent as that of fluticasone (FIG. 6a). The peribronchial inflammation score was also significantly decreased by inhalation of Compound I-HPβCD containing formulations as well as by fluticasone (p<0.0001) (FIG. 6b). The tissue eosinophil infiltration score was also decreased after treatment by Compound I inhalation in an extent comparable to the fluticasone treated mice (p<0.01) (FIG. 6c).

LIST OF REFERENCES

Bergers, G., et al., Nat. Cell Biol. 2 (2000) 737-744
Boroujerdi, M., Pharmacokinetics, Principles and Applications. McGrow-Hill Companies, USA, 2002
Carmeliet, P., et al., Nat. Genet. 17 (1997) 439-444
Carstanjen, D., et al., Transfusion 42 (2002) 588-596
Cataldo, D. D., et al., Am. J. Pathol. 161 (2002) 491-498
Chang, C., and Werb, D., Trends Cell Biol. 11 (2001) S37-43
Chiap, P., et al., Journal of Chromatography B 817 (2005), 109-117
Dong, Z., et al., Cell 88 (1997) 801-810
Egeblad, M., and Werb, Z., Nat. Rev. Cancer 2 (2002) 161-174
EP 0 869 947
Fabbri, I. M., and Hurd, S. S., Eur. Respir. J. 22 (2003) 1-2
GINA Workshop Report, Global Strategy for Asthma Management and Prevention (NIH Publication No. 02-3659)
Grams, F., et al., Biol. Chem. 382 (2001) 1277-1285
Hamelmann, E., et al., Am. J. Respir. Crit. Care Med. 156 (1997) 766-775
Higuchi, T., and Connors, K. A., Advances in Analytical Chemistry and Instrumentation 4 (1965) 117-212
Holmbeck, K., et al., Cell 99 (1999) 81-92
Hubert, P., et al., Analytica Chimica Acta 391 (1999) 135-148
Hubert, Ph., et al., J. Pharm. Biomed. Anal. 36 (2004) 579-586
Hubert, Ph., et al., S. T. P. Pharma Pratiques 9 (1999) 160-180
Hubert, Ph., et al., S. T. P. Pharma Pratiques 13 (2003) 27-64
Lund, L. R., et al., EMBO J. 18 (1999) 4645-4656
Manes, S., et al., J. Biol. Chem. 274 (1999) 6935-6945
Overall, C. M., and Lopez-Otin, C., Nat. Rev. Cancer 2 (2002) 657-672
Remington's Pharmaceutical Sciences, 16th ed., 1980, Mack Publishing Co., edited by Oslo et al.
Shapiro, S. D., Curr. Opin. Cell Biol. 10 (1998) 602-608
Souverain, S., et al., Journal of Chromatography B 801 (2004) 141-156
U.S. Pat. No. 6,110,924
U.S. Pat. No. 6,242,455
Vu, T. H., et al., Cell 93 (1998) 411-422
WO 01/25217
WO 97/23465
WO 98/58915
Yu, Z., and Westerlund, D., Chromatographia 44 (1997) 589-594

The invention claimed is:

1. A trioxopyrimidine-cyclodextrin complex formed of a trioxopyrimidine derivative or a salt thereof and a water-soluble cyclodextrin, wherein the trioxopyrimidine derivative is a compound by formula (I):

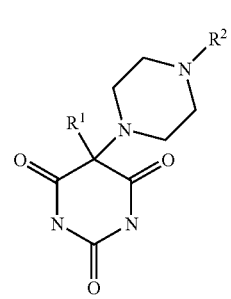

wherein
$R^1$ is $C_3$-$C_{20}$ alkyl, which may optionally be interrupted once or several times by —S—, —O— or —NH—; or a group W-V, wherein
  W is a chemical bond or phenyl; and
  V is phenyl, phenyloxy, phenylthio, phenylsulfinyl, phenylsulfonyl or phenylamino, which phenyl moieties may be unsubstituted or substituted once or several times by halogen, hydroxy, $C_1$-$C_6$ alkyl, $C_1$-$C_6$ alkoxy, $C_1$-$C_6$-alkylthio, $C_1$-$C_6$ alkylsulfinyl, $C_1$-$C_6$-alkylamino, cyano, nitro or $C_1$-$C_6$-alkylsulfonyl; and
$R^2$ is $C_1$-$C_{10}$ alkyl, which alkyl group is unsubstituted or substituted one or two times by hydroxy or amino and may optionally be interrupted once or several times by —S—, —O— or —NH—;
  a benzoyl group, which may be unsubstituted or substituted once or several times by halogen, hydroxy, nitro, $C_1$-$C_6$-alkylsulfinyl, $C_1$-$C_6$-alkylsulfonyl, amidosulfonyl, $C_1$-$C_6$-alkylamidosulfonyl, bis-$C_1$-$C_6$-alkylamidosulfonyl;
  a heteroaromatic acyl group; or
  a phenyl- or heteroaryl group, which are unsubstituted or substituted once or several times by halogen, hydroxyl, $C_1$-$C_6$-aloxy, $C_1$-$C_6$-alkylamino, $C_1$-$C_6$-dialkylamino, cyano, $C_1$-$C_6$-alkyl, $C_2$-$C_6$ alkinyl, $C_1$-$C_6$-acyl, $C_1$-$C_6$-alkylthio, $C_1$-$C_6$-alkylsulfonyl, $C_1$-$C_6$-alkylsulfinyl, $C_1$-$C_6$-alkyl-aminocarbonyl, aminocarbonyl, $C_1$-$C_6$-alkylamidosulfonyl, amidosulfonyl, bis-$C_1$-$C_6$-alkylamidosulfonyl, nitro, $C_1$-$C_6$-alkoxycarbonyl, carboxy; and
wherein the trioxopyrimidine derivative is
  5-Biphenyl-4-yl-5[4-(4-nitro-phenyl)-piperazin-1-yl] pyrimidine-2,4,6-trione;
  5-(4-Phenoxy-phenyl)-5-(4-pyrimidin-2-yl-piperazin-1-yl)-pyrimidine-2,4,6-trione;
  5[4-(4-Chloro-phenoxy)-phenyl]-5-(4-pyrimidin-2-yl-piperazin- -1-yl)- pyrimidine-2,4,6-trione;
  5-[4-(3,4-Dichloro-phenoxy)-phenyl]-5-(4-pyrimidin-2-yl-piperazin-1-yl)- pyrimidine-2,4,6-trione;
  5-[4-(4-Bromo-phenoxy)-phenyl]-5-(4-pyrimidin-2-yl-piperazin-1-yl)- pyrimidine-2,4,6-trione
  or a salt thereof.

2. A trioxopyrimidine-cyclodextrin complex according to claim 1, wherein L-Lysine or L-arginine is added as adjuvant.

3. The trioxopyrimidine-cyclodextrin complex according to claim 1, wherein the water-soluble cyclodextrin is β-cyclodextrin.

4. The trioxopyrimidine-cyclodextrin complex according to claim 1, wherein the water-soluble cyclodextrin is hydroxypropylated cyclodextrin.

5. The trioxopyrimidine-cyclodextrin complex according to claim 1, wherein the water-soluble cyclodextrin is random methylated cyclodextrin.

6. The trioxopyrimidine-cyclodextrin complex according to claim 1, wherein the water-soluble cyclodextrin is sulfobutyl-β-cyclodextrin.

7. The trioxopyrimidine-cyclodextrin complex according to claim 1, wherein the water-soluble cyclodextrin is γ-cyclodextrin.

8. A pharmaceutical composition containing the trioxopyrimidine-cyclodextrin complex according to claim 1 and one or more pharmaceutically acceptable additives.

9. The pharmaceutical composition according to claim 8 wherein the trioxopyrimidine derivative is 5-Biphenyl-4-yl-5-[4-(4-nitro-phenyl)-piperazin-1-yl]pyrimidine-2,4,6-trione;
5-(4-Phenoxy-phenyl)-5-(4-pyrimidin-2-yl-piperazin-1-yl)-pyrimidine-2,4,6-trione;
5-[4-(4-Chloro-phenoxy)-phenyl]-5-(4-pyrimidin-2-yl-piperazin- -1-yl)- pyrimidine-2,4,6-trione;
5-[4-(3,4-Dichloro-phenoxy)-phenyl]-5-(4-pyrimidin-2-yl-piperazin-1-yl)- pyrimidine-2,4,6-trione;
5-[4-(4-Bromo-phenoxy)-phenyl]-5-(4-pyrimidin-2-yl-piperazin-1-yl)- pyrimidine-2,4,6-trione or a salt thereof.

* * * * *